(12) United States Patent
Jones et al.

(10) Patent No.: US 8,080,573 B2
(45) Date of Patent: Dec. 20, 2011

(54) HETEROCYCLE SUBSTITUTED AMIDE AND SULFUR AMIDE DERIVATIVES AS HISTONE DEACETYLASE (HDAC) INHIBITORS

(75) Inventors: Philip Jones, Rome (IT); Jesus Maria Ontoria Ontoria, Pomezia (IT)

(73) Assignee: Istituto Di Ricerche Di Biologia Molecolare P. Angeletti SpA, Pomezia, Rome (IT)

( * ) Notice: Subject to any disclaimer, the term of this patent is extended or adjusted under 35 U.S.C. 154(b) by 483 days.

(21) Appl. No.: 12/084,269

(22) PCT Filed: Oct. 26, 2006

(86) PCT No.: PCT/GB2006/050353
§ 371 (c)(1),
(2), (4) Date: Nov. 14, 2008

(87) PCT Pub. No.: WO2007/052073
PCT Pub. Date: May 10, 2007

(65) Prior Publication Data
US 2009/0156619 A1   Jun. 18, 2009

(30) Foreign Application Priority Data
Oct. 31, 2005 (GB) .................................. 0522130.4

(51) Int. Cl.
*A61K 31/4164* (2006.01)
*C07D 233/54* (2006.01)
(52) U.S. Cl. .............. 514/396; 548/311.1; 548/312.1; 548/335.1; 548/338.1; 514/385; 514/397
(58) Field of Classification Search ............... 548/311.1, 548/312.1, 335.1, 338.1; 514/385, 396, 397
See application file for complete search history.

(56) References Cited

U.S. PATENT DOCUMENTS

| | | | |
|---|---|---|---|
| 6,852,725 B1 * | 2/2005 | Thurieau et al. | 514/254.08 |
| 7,238,695 B2 * | 7/2007 | Thurieau et al. | 514/254.05 |
| 7,566,734 B2 * | 7/2009 | Thurieau et al. | 514/399 |
| 7,638,546 B1 * | 12/2009 | Thurieau et al. | 514/400 |
| 2004/0122079 A1 | 6/2004 | Grossmann et al. | |
| 2004/0157841 A1 | 8/2004 | Fertig et al. | |
| 2008/0221157 A1 | 9/2008 | Chakravarty et al. | |

FOREIGN PATENT DOCUMENTS

| | | |
|---|---|---|
| EP | 1 209 147 | 5/2002 |
| JP | 58 029780 | 2/1983 |
| WO | WO 98/27108 | 6/1998 |
| WO | WO 99/64401 | 12/1999 |
| WO | WO 02/10140 | 2/2002 |
| WO | WO 2004/072047 | 8/2004 |
| WO | WO 2006/004924 | 1/2006 |
| WO | WO 2006/005955 | 1/2006 |
| WO | WO 2006/061638 | 6/2006 |

OTHER PUBLICATIONS

Thurieau et al (1999): STN International HCAPLUS database, (Columbus, Ohio), Accession No. 1999:795794.*
Miller, et al., J. Med. Chem, vol. 46, p. 5097 (2003).
Arts, et al., Cuff. Med. Chem., vol. 10, p. 2343 (2003).
Notice of Allowance mailed Aug. 26, 2010 in U.S. Appl. No. 11/792,294.

* cited by examiner

*Primary Examiner* — Golam M M Shameem
(74) *Attorney, Agent, or Firm* — Li Su; David A. Muthard

(57) ABSTRACT

The present invention related to compounds of formula (I): or a pharmaceutically acceptable salt, stereoisomer or tautomer thereof. Compounds of the present invention are inhibitors of histone deacetylase (HDAC) and are useful for treating cellular proliferative diseases, including cancer. Compounds of the present invention are useful for treating or preventing neurodegenerative diseases, schizophrenia and stroke among other diseases.

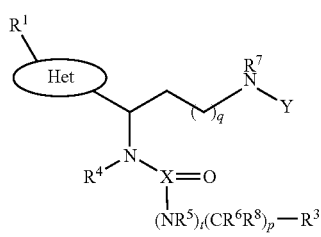

(I)

6 Claims, No Drawings

HETEROCYCLE SUBSTITUTED AMIDE AND SULFUR AMIDE DERIVATIVES AS HISTONE DEACETYLASE (HDAC) INHIBITORS

PRIORITY CLAIM

This application is a §371 National Stage Application of PCT/GB2006/050353, filed on Oct. 26, 2006, which claims priority from GB Provisional Application Serial Number 0522130.4, filed on Oct. 31, 2005.

BACKGROUND OF THE INVENTION

In eukaryotic cells the orderly packaging of DNA in the nucleus plays an important role in the regulation of gene transcription. Nuclear DNA is ordered in a compact complex called chromatin. The core of the complex is an octamer of highly conserved basic proteins called histones. Two each of histones H2A, H2B, H3 and H4 associate and DNA winds around the basic amino acids of the histones interacting with the negatively charged phosphate groups of the DNA. One molecule of histone H1 is associated with each wound core which accommodates approximately 146 bp of DNA. The cores are, in turn, packaged into a compact regular structure with about 200 bp of DNA between each core.

The amino-terminal tails of the histones are subject to post-translational modification, in particular by acetylation of lysine. Histone deacetylases (HDACs) and histone acetyl transferases (HATs) determine the pattern of histone acetylation, which together with other dynamic sequential post-translational modifications might represent a 'code' that can be recognised by non-histone proteins forming complexes involved in the regulation of gene expression. This and the ability of histone deacetylases (HDACs) to also modify non-histonic substrates and participate in multi-protein complexes contributes to the regulation of gene transcription, cell cycle progression and differentiation, genome stability and stress responses.

Eleven members of the HDAC family have been identified in humans, which share a conserved catalytic domain and are grouped into two classes: class I (1, 2, 3, 8), homologous to yeast Rpd3; class IIa (4, 5, 7, 9) and IIb (6, 10), homologous to yeast Hda1. HDAC11 shares homologies with both classes, but is at the same time distinct from all the other ten subtypes. Interest in these enzymes is growing because HDAC inhibitors (HDACi) are promising therapeutic agents against cancer and other diseases. The first generation of HDACi were discovered from cell-based functional assays and only later identified as HDAC class I/II inhibitors. Present HDAC inhibitors are pan-specific or poorly selective. Those that entered clinical trials all show similar adverse effects, mainly fatigue, anorexia, hematologic and GI-toxicity, that becomes dose-limiting in clinical trials. It is not at all clear whether the antitumor properties of HDAC inhibitors are due to their lack of specificity or are the consequence of hitting one or few "crucial" subtypes. This question is of considerable interest because it may open the way for the development of novel, more sensitive compounds with possibly enhanced efficacy and/or tolerability. More recent studies were therefore directed to better define the biological function of different class members and to devise subtype-selective enzymatic assays to assist in the development of improved cancer chemotherapies.

The class IIa HDACs contain a highly conserved C-terminal catalytic domain (~420 amino acids) homologous to yHDA1 and an N-terminal domain with no similarity to other proteins. The activity of the class IIa HDACs is regulated at several levels, including tissue-specific gene expression, recruitment of distinct cofactors and nucleocytoplasmic shuttling. Whereas most class I HDACs are ubiquitously expressed, class IIa HDACs are expressed in a restricted number of cell types.

HDAC inhibitors cause the induction of differentiation, growth arrest and/or apoptosis in a broad spectrum of transformed cells in culture and tumours in animals, including both haematological cancers and solid tumours. These inhibitory effects are believed to be caused, in part, by accumulation of acetylated proteins, such as nucleosomal histones, which appear to play a major role in regulation of gene transcription. A proposed mechanism for the anti-tumour effects of HDAC inhibitors is that the accumulation of acetylated histones leads to activation (and repression) of the transcription of a select number of genes whose expression causes inhibition of tumour cell growth. Expression profiling of cells cultured with HDAC inhibitors supports this model, as studies demonstrate that the expression of a small number of genes (2-5% of the expressed genes) is altered (activated or repressed). The mechanism of gene repression or activation is not well understood and might result from either direct or indirect effects of histone acetylation or from the increase in acetylation of proteins other than histones (e.g. transcription factors).

There is still much to be understood about the family of HDACs, including the varying functions of different HDACs and the range of HDAC substrates. The development of selective HDAC inhibitors might be important in defining their biological role and potential as therapeutic agents. Clinically, the optimal dose, timing and duration of therapy, as well as the most appropriate agents to combine with HDAC inhibitors, are still to be defined.

SUMMARY OF INVENTION

WO 99/64401 and WO 02/10140 disclose imidazolyl derivatives as somatostatin receptor agonists and antagonists.

The compounds of this invention are useful in the inhibition of histone deacetylase, particularly class I histone deacetylase. The compounds are HDAC 1, HDAC 2 and HDAC 3 inhibitors.

The present invention provides the use of a compound of formula I:

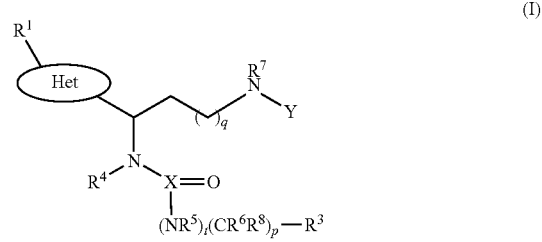

(I)

wherein:
p is 0, 1, 2 or 3;
q is 1, 2, 3 or 4;
t is 0 or 1;
X is C or S=O;
Y is $R^2$, $(C=S)R^2$, $(C=O)R^2$, $(C=S)NR^xR^2$ or $(C=O)NR^xR^2$;
Het is a 5 membered unsaturated heterocycle containing 1, 2, 3 or 4 heteroatoms independently selected from N, O and S, but not more than one of which is O or S, or a 6 membered unsaturated heterocycle containing 1, 2, 3 or 4 heteroatoms independently selected from N and O; optionally substituted by one or more groups independently chosen from cyano, halogen, hydroxy, oxido, oxo, nitro, amino, $C_{1-6}$alkylamino, di($C_{1-6}$alkyl)amino, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;

$R^1$ is hydrogen, $C_{1-6}$alkyl, halo$C_{1-6}$alkyl, $C_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated or partially saturated heterocycle containing heteroatoms independently selected from O, N and S; any of which rings being optionally substituted by one or more groups independently chosen from cyano, halogen, nitro, oxo, hydroxy, oxido, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$alkoxy, $C_{6-10}$arylcarbonyl, $N(R^a)_2$, $SO_2N(R^b)_2$ and $N(R^b)SO_2R^b$;

$R^2$ is $R^9$ or $R^{10}$;

$R^3$ is hydrogen, halogen, hydroxy, cyano, $C_{1-6}$alkyl, halo$C_{1-6}$alkyl, hydroxy$C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, $N(R^c)_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen from $R^d$;

$R^4$, $R^5$ and $R^7$ are independently selected from hydrogen and $C_{1-6}$alkyl;

$R^6$ and $R^8$ are independently hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl; or $R^6$ and $R^8$ together represent an oxo group;

$R^9$ is hydrogen, hydroxy, $C_{1-6}$alkyl, halo$C_{1-6}$alkyl or $C_{1-6}$alkoxy;

$R^{10}$ is $C_{6-10}$aryl, $C_{6-10}$aryl$C_{1-6}$alkyl, a 5 membered unsaturated heterocycle containing 1, 2, 3 or 4 heteroatoms independently selected from N, O and S, but not more than one of which is O or S, or a 6 membered unsaturated heterocycle containing 1, 2, or 3 heteroatoms independently selected from N and O; optionally substituted by one or more groups independently chosen from cyano, halogen, hydroxy, oxo, oxido, nitro, $N(R^e)_2$, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl, CON$(R^b)_2$, $NR^bCOR^b$, $SO_2N(R^b)_2$, $NR^bSO_2R^b$, $C_{6-10}$aryl, 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from N, O and S, but not more than one of which is O or S, 6 membered unsaturated heterocycle containing 1, 2 or 3 nitrogen atoms and a 7-10 membered saturated, partially saturated or unsaturated heterocycle containing heteroatoms independently selected from N, O or S;

each $R^a$ is independently selected from hydrogen, $C_{1-6}$alkyl, $C_{6-10}$aryl, $C_{1-6}$alkylcarbonyl and $C_{6-10}$arylcarbonyl;

each $R^b$ is independently hydrogen, $C_{1-6}$alkyl, $C_{2-6}$alkenyl, $C_{2-6}$alynyl, $C_{6-10}$aryl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy, each $R^c$ is independently selected from hydrogen and $C_{1-4}$alkyl;

each $R^d$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, $SO_2N(R^e)$, $NR^eSO_2R^e$, $N(R^e)$, $C_{6-10}$aryl, $C_{6-10}$aryl$C_{1-6}$alkyl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

each $R^e$ is independently hydrogen, $C_{1-6}$alkyl, $C_{1-6}$alkylcarbonyl, carboxy or $C_{1-6}$alkyloxycarbonyl; and each $R^x$ is independently selected from hydrogen and $C_{1-6}$alkyl;

or a pharmaceutically acceptable salt, stereoisomer or tautomer thereof, for the manufacture of a medicament for the treatment or prevention of neurodegenerative diseases, schizophrenia, stroke, mental retardation, immune disorders or asthma.

The present invention also provides a method for the treatment or prevention of neurodegenerative diseases, schizophrenia, stroke, mental retardation, immune disorders or asthma, which method comprises administration to a patient in need thereof of an effective amount of a compound of formula I or composition comprising a compound of formula I.

In another aspect of the present invention is provided novel compounds of formula I:

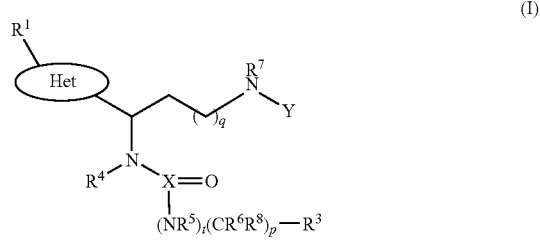

wherein:

p is 0, 1, 2 or 3;

q is 1, 2, 3 or 4;

t is 0 or 1;

X is C or S=O;

Y is $R^2$, (C=S)$R^2$, (C=O)$R^2$, (C=S)NR$^x$R$^2$ or (C=O)NR$^x$R$^2$;

Het is a 5 membered unsaturated heterocycle containing 1, 2, 3 or 4 heteroatoms independently selected from N, O and S, but not more than one of which is O or S, or a 6 membered unsaturated heterocycle containing 1, 2, 3 or 4 heteroatoms independently selected from N and O; optionally substituted by one or more groups independently chosen from cyano, halogen, hydroxy, oxido, oxo, nitro, amino, $C_{1-6}$alkylamino, di($C_{1-6}$alkyl)amino, $C_{1-6}$alkyl, halo$C_{6-10}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;

$R^1$ is hydrogen, $C_{1-6}$alkyl, halo$C_{1-6}$alkyl, $C_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated or partially saturated heterocycle containing heteroatoms independently selected from O, N and S; any of which rings being optionally substituted by one or more groups independently chosen from cyano, halogen, nitro, oxo, hydroxy, oxido, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl, N($R^a$)$_2$, SO$_2$N($R^b$)$_2$ and N($R^b$)SO$_2$R$^b$;

$R^2$ is $R^9$ or $R^{10}$;

$R^3$ is hydrogen, halogen, hydroxy, cyano, $C_{1-6}$alkyl, halo$C_{1-6}$alkyl, hydroxy$C_{1-6}$alkyl, $C_{1-6}$alkoxy, halo$C_{1-6}$alkoxy, $C_{3-10}$cycloalkyl, halo$C_{3-10}$cycloalkyl, $C_{2-10}$alkenyl, $C_{2-10}$alkynyl, nitro, N($R^c$)$_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen from $R^d$;

$R^4$, $R^5$ and $R^7$ are independently selected from hydrogen and $C_{1-6}$alkyl;

$R^6$ and $R^8$ are independently hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl; or $R^6$ and $R^8$ together represent an oxo group;

$R^9$ is hydrogen, hydroxy, $C_{1-6}$alkyl, halo$C_{1-6}$alkyl or $C_{1-6}$alkoxy, $R^{10}$ is $C_{6-10}$aryl, $C_{6-10}$aryl$C_{1-6}$alkyl, a 5 membered unsaturated heterocycle containing 1, 2, 3 or 4 heteroatoms independently selected from N, O and S, but not more than one of which is O or S, or a 6 membered unsaturated heterocycle containing 1, 2, or 3 heteroatoms independently selected from N and O; optionally substituted by one or more groups independently chosen from cyano, halogen, hydroxy, oxo, oxido, nitro, N($R^c$)$_2$, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl, CON($R^b$)$_2$, NR$^b$COR$^b$, SO$_2$N($R^b$)$_2$, NR$^b$SO$_2$R$^b$, $C_{6-10}$aryl, 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from N, O and S, but not more than one of which is O or S, 6 membered unsaturated heterocycle containing 1, 2 or 3 nitrogen atoms and a 7-10 membered saturated, partially saturated or unsaturated heterocycle containing heteroatoms independently selected from N, O or S;

each $R^a$ is independently selected from hydrogen, $C_{1-6}$alkyl, $C_{6-10}$aryl, $C_{1-6}$alkylcarbonyl and $C_{6-10}$arylcarbonyl;

each $R^b$ is independently hydrogen, $C_{1-6}$, $C_{2-6}$alkenyl, $C_{2-6}$alkynyl, $C_{6-10}$aryl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

each $R^c$ is independently selected from hydrogen and $C_{1-6}$alkyl;

each $R^d$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, SO$_2$N($R^e$)$_2$, NR$^3$SO$_2$R$^e$, N($R^e$)$_2$, $C_{6-10}$aryl, $C_{6-10}$aryl$C_{1-6}$alkyl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

each $R^e$ is independently hydrogen, $C_{1-6}$alkyl, $C_{1-6}$alkylcarbonyl, carboxy or $C_{1-6}$alkyloxycarbonyl; and each $R^x$ is independently selected from hydrogen and $C_{1-6}$alkyl;

provided that when Y is $R^2$ then $R^9$ is not hydrogen or $C_{1-6}$alkyl; and when Y is (C=O)$R^2$ then $R^9$ is not hydroxy or $C_{1-6}$alkoxy;

or a pharmaceutically acceptable salt, stereoisomer or tautomer thereof.

In another embodiment of the present invention is provided compounds of formula I wherein:

p is 0, 1, 2 or 3;

q is 1, 2, 3 or 4;

t is 0 or 1;

X is C or S=O;

Y is $R^{10}$, (C=S)$R^2$, (C=O)$R^{10}$, (C=S)NR$^x$R$^2$ or (C=O)NR$^x$R$^2$;

Het is a 5 membered unsaturated heterocycle containing 1, 2, 3 or 4 heteroatoms independently selected from N, O and S, but not more than one of which is O or S, or a 6 membered unsaturated heterocycle containing 1, 2, 3 or 4 heteroatoms independently selected from N and O; optionally substituted by one or more groups independently chosen from cyano, halogen, hydroxy, oxido, oxo, nitro, amino, $C_{1-6}$alkylamino, di($C_{1-6}$alkyl)amino, $C_{1-6}$alkyl, halo$C_{1-6}$, $C_{1-6}$alkoxy, halo$C_{1-6}$ alkoxy, $C_{3-10}$cycloalkyl, $C_{2-6}$alkenyl, $C_{2-6}$alkynyl and $C_{6-10}$aryl;

$R^1$ is hydrogen, $C_{1-6}$alkyl, halo$C_{1-6}$alkyl, $C_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated or partially saturated heterocycle containing heteroatoms independently selected from O, N and S; any of which rings being optionally substituted by one or more groups independently chosen from cyano, halogen, nitro, oxo, hydroxy, oxido, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl, $N(R^a)_2$, $SO_2N(R^b)_2$ and $N(R^b)SO_2R^b$;

$R^2$ is $R^9$ or $R^{10}$;

$R^3$ is hydrogen, halogen, hydroxy, cyano, $C_{1-6}$alkyl, halo$C_{1-6}$alkyl, hydroxy$C_{1-6}$alkyl, $C_{1-6}$alkoxy, halo$C_{1-6}$ alkoxy, $C_{3-10}$cycloalkyl, halo$C_{3-10}$cycloalkyl, $C_{2-10}$alkenyl, $C_{2-10}$alkynyl, nitro, $N(R^c)_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen from $R^d$;

$R^4$, $R^5$ and $R^7$ are independently selected from hydrogen and $C_{1-6}$alkyl;

$R^6$ and $R^8$ are independently hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl; or $R^6$ and $R^8$ together represent an oxo group;

$R^9$ is hydrogen, hydroxy, $C_{1-6}$alkyl, halo$C_{1-6}$alkyl or $C_{1-6}$alkoxy, $R^{10}$ is $C_{6-10}$aryl, $C_{6-10}$aryl$C_{1-6}$alkyl, a 5 membered unsaturated heterocycle containing 1, 2, 3 or 4 heteroatoms independently selected from N, O and S, but not more than one of which is O or S, or a 6 membered unsaturated heterocycle containing 1, 2, or 3 nitrogen atoms independently selected from N and O; optionally substituted by one or more groups independently chosen from cyano, halogen, hydroxy, oxo, oxido, nitro, $N(R^c)_2$, $C_{1-6}$alkyl, halo$C_{1-6}$alkyl, $C_{1-6}$alkoxy, halo$C_{1-6}$ alkoxy, $C_{3-10}$cycloalkyl, $C_{2-6}$alkenyl, $C_{2-6}$alkynyl, CON$(R^b)_2$, $NR^bCOR^b$, $SO_2N(R^b)_2$, $NR^bSO_2R^b$, $C_{6-10}$aryl, 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from N, O and S, but not more than one of which is O or S, 6 membered unsaturated heterocycle containing 1, 2 or 3 nitrogen atoms and a 7-10 membered saturated, partially saturated or unsaturated heterocycle containing heteroatoms independently selected from N, O or S;

each $R^a$ is independently selected from hydrogen, $C_{1-6}$alkyl, $C_{6-10}$aryl, $C_{1-6}$alkylcarbonyl and $C_{6-10}$arylcarbonyl;

each $R^b$ is independently hydrogen, $C_{1-6}$alkyl, $C_{2-6}$alkenyl, $C_{2-6}$alkynyl, $C_{6-10}$aryl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$, halo$C_{1-6}$alkyl, $C_{1-6}$alkoxy and halo$C_{1-6}$alkoxy, each $R^c$ is independently selected from hydrogen and $C_{1-6}$alkyl;

each $R^d$ is halogen, hydroxy, cyano, $C_{1-6}$alkyl, halo$C_{1-6}$ alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, $SO_2N(R^e)_2$, $NR^eSO_2R^e$, $N(R^e)_2$, $C_{6-10}$aryl, $C_{6-10}$aryl$C_{1-6}$alkyl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

each $R^e$ is independently hydrogen, $C_{1-6}$alkyl, $C_{1-6}$alkylcarbonyl, carboxy or $C_{1-6}$alkyloxycarbonyl; and each $R^x$ is independently selected from hydrogen and $C_{1-6}$alkyl;

or a pharmaceutically acceptable salt, stereoisomer or tautomer thereof.

In a preferred embodiment of each one of the previous embodiments:

$R^1$ is hydrogen, $C_{1-6}$alkyl, halo$C_{1-6}$alkyl, $C_{6-10}$aryl, 5 membered unsaturated heterocycle containing 1, 2, 3 or 4 heteroatoms independently selected from O, N and S, but not more than one of which is O or S, 6 membered unsaturated heterocycle containing 1, 2 or 3 nitrogen atoms, or 8-10 membered unsaturated or partially saturated heterocycle containing heteroatoms independently selected from O, N and S; any of which rings being optionally substituted by one or more groups independently chosen from cyano, halogen, nitro, oxo, hydroxy, oxido, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl and $N(R^a)_2$ wherein $R^a$ is independently selected from hydrogen, $C_{1-6}$alkyl, $C_{6-10}$aryl, $C_{1-6}$alkylcarbonyl and $C_{6-10}$arylcarbonyl;

$R^{10}$ is $C_{6-10}$aryl, $C_{6-10}$aryl$C_{1-6}$alkyl, a 5 membered unsaturated heterocycle containing 1, 2, 3 or 4 heteroatoms independently selected from N, O and S, but not more than one of which is O or S, or a 6 membered unsaturated heterocycle containing 1, 2, or 3 nitrogen atoms independently selected from N and O; optionally substituted by one or more groups independently chosen from cyano, halogen, hydroxy, oxo, oxido, nitro, $N(R^c)$, $C_{1-6}$alkyl, halo$C_{1-6}$alkyl, $C_{1-6}$alkoxy, halo$C_{1-6}$ alkoxy, $C_{3-10}$cycloalkyl, $C_{2-6}$alkenyl, $C_{2-6}$alkynyl and $C_{6-10}$aryl; and each $R^d$ is halogen, hydroxy, cyano, $C_{1-6}$alkyl, halo$C_{1-6}$ alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, $SO_2N(R^e)_2$, $N(R^e)_2$ wherein $R^e$ is independently selected from hydrogen, $C_{1-6}$alkyl, $C_{1-6}$alkylcarbonyl, carboxy and $C_{1-6}$alkyloxycarbonyl; $C_{6-10}$aryl, $C_{6-10}$aryl$C_{1-6}$alkyl, 5 or 6 membered saturated or partially saturated heterocycle containing 1, 2 or 3 heteroatoms independently selected from N, O or S, optionally bridged by a $C_{1-6}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy.

p is preferably 0, 1 or 2. In one embodiment p is 1 or 2.

q is preferably 2, 3 or 4, especially 3 or 4, and most especially 3.

In one embodiment t is 0.

In another embodiment t is 1 and $R^5$ is hydrogen or methyl, preferably methyl.

In an embodiment of the present invention X is C.

In another embodiment X is S=O.

In an embodiment, Y is (C=S)$R^2$, (C=S)N$R^x R^2$ or (C=O)N$R^x R^2$.

In an embodiment Y is (C=O)N$R^x R^2$.

Preferably, $R^x$ is hydrogen or methyl, particularly hydrogen.

In an embodiment Y is $R^{10}$ or (C=O)$R^{10}$.

Preferably, Het is an optionally substituted 5 membered unsaturated heterocycle containing 1, 2 or 3 heteroatoms independently selected from N, O and S, but not more than one of which is O or S, or an optionally substituted 6 membered unsaturated heterocycle containing 1, 2 or 3 nitrogen atoms.

In one embodiment Het is an optionally substituted 5 membered unsaturated heterocycle containing 1, 2, 3 or 4 heteroatoms independently selected from N, O and S, but not more than one of which is O or S.

More particularly Het is an optionally substituted imidazolyl, oxazolyl, triazolyl, thienyl, furyl, oxadiazolyl, thiazolyl, pyrazolyl or pyridinyl.

Preferably Het is unsubstituted or substituted by one, two or three groups. More particularly Het is unsubstituted or monosubstituted Favoured optional substituents include $C_{1-6}$alkyl and $C_{6-10}$aryl, especially methyl and phenyl.

In one embodiment Het is unsubstituted.

For the avoidance of doubt $R^1$ may be attached to any substitutable position of Het as may any optional substituent on Het.

Thus, particular preferred Het groups include imidazolyl, methylimidazolyl, phenylimidazolyl, phenyloxazolyl, triazolyl, thienyl, furyl, oxadiazolyl, thiazolyl, oxazolyl, pyrazolyl and pyridinyl.

In an embodiment Het is imidazolyl.

Specific Het groups are imidazol-2-yl, 4-methylimidazol-2-yl, 4-phenylimidazol-2-yl, 4 phenyloxazol-2-yl, 1,2,4-triazol-3-yl, 1-methylimidazol-2-yl, 2-thienyl, 2-furyl, 1,3,4-oxadiazol-2-yl, 1,3-thiazol-2-yl, 1,2,4-oxadiazol-5-yl, 1,3-thiazol-5-yl, 1,2,4-oxadiazol-3-yl, 1,3-oxazol-2-yl, imidazol-4-yl, pyrazol-5-yl and pyridin-2-yl.

In an embodiment Het is imidazol-2-yl.

Preferably, $R^1$ is an optionally substituted ring selected from $C_{6-10}$aryl, a 5 membered unsaturated heterocycle containing 1, 2 or 3 heteroatoms independently selected from N, O and S, but not more Oman one of which is O or S, a 6 membered unsaturated heterocycle containing 1, 2 or 3 nitrogen atoms, or a 8, 9 or 10 membered unsaturated or partially saturated heterocycle containing 1, 2, 3 or 4 heteroatoms independently selected from O, N and S.

More particularly, $R^1$ is an optionally substituted phenyl, naphthyl, thienyl, isoxazolyl, pyridinyl, benzothienyl, thiazolotriazolyl, dihydrobenzodioxinyl, benzothiazolyl, quinolinyl or isoquinolinyl.

Favourably $R^1$ is unsubstituted or substituted by one, two or three groups. More particularly $R^1$ is unsubstituted, monosubstituted or disubstituted. Favoured optional substituents include cyano, halogen, $C_{1-4}$alkyl, halo$C_{1-4}$-alkyl, $C_{1-4}$alkoxy, halo$C_{1-4}$alkoxy and $C_{6-10}$aryl. Examples of typical optional substituents include cyano, bromine, chlorine, fluorine, methyl, trifluoromethyl, methoxy, difluoromethoxy, trifluoromethoxy and phenyl.

In an embodiment $R^1$ is unsubstituted.

Thus, particular preferred $R^1$ groups include phenyl cyanophenyl bromophenyl, chlorophenyl, dichlorophenyl, fluorophenyl, difluorophenyl, trifluoromethylphenyl, bis(trifluoromethyl)phenyl, methoxyphenyl, difluoromethoxyphenyl, biphenyl, naphthyl, thienyl phenylisoxazolyl, pyridinyl, (chloro)(methyl)benzothienyl, (methyl)(trifluoromethyl)thiazolotriazolyl benzothienyl dihydrobenzodioxinyl, benzothiazolyl, methoxyquinolinyl, quinolinyl and isoquinolinyl.

In an embodiment $R^1$ is naphthyl.

Specific $R^1$ groups are phenyl, 3-cyanophenyl, 4-cyanophenyl, 4bromophenyl, 2-chlorophenyl, 3-chlorophenyl, 4-chlorophenyl, 3,4--dichlorophenyl, 4-fluorophenyl, 3,4-difluorophenyl, 3-(trifluoromethyl)phenyl, 4-trifluoromethyl)phenyl, 3,5-bis(trifluoromethyl)phenyl, 2-methoxyphenyl, 3-methoxyphenyl, 4-difluoromethoxy)phenyl, biphenyl, 2-naphthyl, 3-thienyl, 3-phenylisoxazol-5-yl, 2-pyridinyl, 5-chloro-3-methyl-1-benzothien-2-yl, 6-methyl-2-trifluoromethyl)[1,3]thiazolo[3,2-b][1,2,4]triazol-5-yl, 1-benzothien-3-yl, 3,5-dichlorophenyl, 2,3-dihydro-1,4-benzodioxin-yl, 2,3-dihydro-1,4-benzodioxin-5-yl, 1,3-benzothiazol-2-yl, 1-benzothien-2-yl, 4-methoxyquinolin-2-yl, quinolin-3-yl, quinolin-yl quinolin-2-yl and isoquinolin-3-yl. A further $R^1$ group is 2-methoxyquinolin-3-yl.

In an embodiment $R^1$ is 2-naphthyl.

In an embodiment $R^2$ is $R^9$.

In another embodiment $R^2$ is $R^{10}$.

$R^2$ is preferably hydrogen, hydroxy, $C_{1-6}$alkyl, halo$C_{1-6}$alkyl, $C_{1-6}$alkoxy or an optionally substituted ring selected from phenyl, benzyl, thienyl, thiazolyl, thiadiazolyl and pyridinyl.

When $R^2$ is a ring, it is preferably unsubstituted or substituted by one, two or three independently selected groups. More particularly, the $R^2$ ring is unsubstituted or monosubstituted.

Preferred optional substituents on the $R^2$ ring are independently selected from amino, hydroxy and oxido. More particularly, the optional substituents are independently selected from amino, hydroxy and oxido.

Particular $R^2$ groups include hydrogen, methyl, hydroxy, aminophenyl, ethyl, isopropyl, methoxy, phenyl, benzyl, thiazolyl, thiadiazolyl, thienyl, propyl, butyl, oxidopyridinyl and ethoxy.

In an embodiment $R^2$ is not hydrogen.

In another embodiment $R^2$ is methyl, thienyl, aminophenyl, methoxy, propyl, butyl, ethyl, oxidopyridinyl, hydroxy or ethoxy.

Specific $R^2$ groups include hydrogen, methyl, hydroxy, 2-aminophenyl, ethyl, isopropyl, methoxy, phenyl, benzyl, 1,3-thiazol-2-yl, 1,3,4-thiadiazol-2-yl, 2-thienyl, propyl, butyl, 2-oxidopyridin-2-yl and ethoxy.

In an embodiment $R^2$ is methyl, 2-thienyl, 2-aminophenyl, methoxy, propyl, butyl, ethyl, 2-oxidopyridin-2-yl, hydroxy, methoxy or ethoxy.

$R^3$ is preferably hydrogen, hydroxy, $C_{1-6}$alkyl, halo$C_{1-6}$alkyl, $C_{1-6}$alkoxy, $C_{3-10}$cycloalkyl, $N(R^c)_2$, $C_{6-10}$aryl, $C_{6-10}$aryl$C_{1-6}$alkoxy; a 5 or 6 membered saturated or partially saturated heterocycle containing 1, 2 or 3 heteroatoms independently selected from N, O and S, optionally bridged by a $C_{1-4}$alkyl group; a 5 membered unsaturated heterocycle containing 1, 2, 3 or 4 heteroatoms independently selected from N, O and S, but not more than one of which is O or S; a 6 membered unsaturated heterocycle containing 1, 2 or 3 nitrogen atoms; or a 8-13 membered saturated, partially saturated or unsaturated heterocycle containing 1, 2, 3 or 4 heteroatoms independently selected from N, O and S; any of which rings being optionally substituted by one or more groups independently chosen from $R^d$.

In an embodiment, $R^3$ is not hydrogen.

In another embodiment, $R^3$ is $N(R^c)_2$ or a 8-10 membered saturated, partially saturated or unsaturated heterocycle containing 1, 2, 3 or 4 heteroatoms independently selected from N, O or S, the ring being optionally substituted by one or more groups independently selected from $R^d$.

$R^c$ is preferably hydrogen, methyl or ethyl. More particularly $R^c$ is hydrogen or methyl.

Particular $R^3$ groups include dimethylamino, phenyl, naphthyl, pyrrolidinyl, piperidinyl, azoniabicyclo[2.2.1]heptanyl, azoniabicyclo[2.2.2]octanyl, piperazinyl, morpholinyl, thienyl, thiazolyl, imidazolyl, pyrazolyl, isoxazolyl, thiadiazolyl, pyridinyl, indolyl, benzothienyl, benzothiadiazolyl, benzoxadiazolyl, dihydrobenzofuryl, dihydrothiazolopyrimidinyl, isoquinolyl, dihydrobenzodioxinyl, dihydrobenzoxazinyl, tert-butoxy, cyclopentyl, methyl, trifluoromethyl, methoxy, methylamino, amino, diethylamino, hydroxy, benzimidazolyl, benzofuranyl, triazolopyrimidinyl, dihydrobenzoxazolyl, dihydroindolyl, dihydroquinazolinyl, dihydrophthalazinyl, indazolyl, quinolinyl, benzisoxazolyl, benzotriazolyl, tetrahydrobetacarbolinyl, dihydroisoindolyl, tetrahydronaphthyridinyl, tetrazolyl, benzyloxy, thiomorpholinyl, azetidinyl, tetrahydroquinolinyl, triazolyl and thiazolidinyl; any of which rings being optionally substituted by one or more groups independently chosen from $R^d$.

In an embodiment $R^3$ is indolyl, benzimidazolyl, dihydroquinazolinyl, dimethylamino or methylamino, any of which rings being optionally substituted by one or more groups independently chosen from $R^d$.

When $R^3$ is a ring, it is preferably unsubstituted or substituted by one, two or three groups selected from $R^d$. In an embodiment the $R^3$ ring is unsubstituted or monosubstituted. In another embodiment the $R^3$ ring is monosubstituted.

Favoured $R^d$ groups include halogen, cyano, $C_{1-6}$alkyl, $C_{1-6}$alkoxy, halo$C_{1-6}$alkoxy, carboxy, $C_{1-6}$alkoxycarbonyl, nitro, aminosulfonyl, ($C_{1-6}$alkylcarbonyl)amino, morpholinyl, piperazinyl, thiazolyl, pyrazolyl, isoxazolyl, pyridinyl, oxo, halo$C_{1-6}$allyl, phenyl and pyrrolidinyl, any of which rings being optionally substituted by one or more groups independently chosen from $C_{1-6}$alkyl and halo$C_{1-6}$alkyl.

In an embodiment $R^d$ is $C_{1-6}$alkyl, $C_{1-6}$alkoxy or oxo.

Particular $R^d$ groups include chlorine, fluorine, cyano, methyl, isopropyl, methoxy, difluoromethoxy, carboxy, nitro, aminosulfonyl, acetylamino, methylpiperazinyl, pyridinyl, methylthiazolyl, (methyl)(trifluoromethyl)pyrazolyl, isoxazolyl, methoxycarbonyl, morpholinyl, bromine, phenyl, oxo, ethyl, trifluoromethyl and pyrrolidinyl.

Specific $R^d$ groups include chlorine, fluorine, cyano, methyl, isopropyl, methoxy, difluoromethoxy, carboxy, nitro, aminosulfonyl, acetylamino, 1-methylpiperazin-4-yl, pyridin-2-yl, 2-methyl-1,3-thiazol-4-yl, 1-methyl-3-trifluoromethyl-1H-pyrazol-5-yl isoxazol-3-yl, methoxycarbonyl morpholin-4-yl bromine, phenyl, oxo, ethyl, trifluoromethyl and pyrrolidin-1-yl.

In an embodiment $R^d$ is methyl, methoxy, ethyl or oxo.

Thus, particular preferred $R^3$ groups include dimethylamino, phenyl, chlorophenyl, fluorophenyl, difluorophenyl, cyanophenyl, (chloro)(cyano)phenyl, (cyano)(fluoro)phenyl, methoxyphenyl, dimethoxyphenyl difluoromethoxyphenyl, carboxyphenyl, nitrophenyl, (fluoro)(nitro)phenyl, acetylaminophenyl, (methylpiperazinyl)phenyl, naphthyl, methylpyrrolidinyl, piperidyl, methylpiperidyl, methylpiperazinyl, azoniabicyclo[2.2.1]heptanyl, pyridinylpiperidyl, thienyl, (methylthiazolyl)thienyl, [(methyl)(trifluoromethyl)pyrazolyl]thienyl, isoxazolylthienyl, chlorothienyl, methoxycarbonylthienyl, thiazolyl, dimethylthiazolyl, (acetylamino)(methyl)thiazolyl, dimethylimidazolyl, trimethylpyrazolyl, dimethylisoxazolyl, methylthiadiazolyl, pyridinyl morpholinylpyridinyl, (methoxy)(methyl)indolyl, benzothienyl, benzothiadiazolyl benzoxadiazolyl, dihydrobenzofuranyl, dihydrothiazolopyrimidinyl, isoquinolyl, dihydrobenzodioxinyl, (methyl)dihydrobenzoxazinyl, aminosulfonylphenyl, cyanopyridinyl, isopropylpiperidinyl, methylmorpholinyl, azoniabicyclo[2.2.2]octanyl, morpholinyl, indolyl, methylindolyl, methoxyindolyl, bromoindolyl, fluoroindolyl, benzimidazolyl, methoxybenzofuranyl, triazolopyrimidinyl, phenylthiazolyl, chlorobenzothienyl, chloroindolyl oxodihydrobenzoxazolyl, methoxyoxohydrodihydroindolyl, ethylbenzimidazolyl, oxodihydroquinazolinyl, methyloxodihydrophthalazinyl, dichlorophenyl, fluoro(trifluoromethyl)phenyl, methylbenzimidazolyl, (trifluoromethyl)benzimidazolyl indazolyl, quinolinyl, benzisoxazolyl, benzotriazolyl, cyanoindolyl, tetrahydrobetacarbolinyl, tert-butoxy, dihydroisoindolyl, tetrahydronaphthyridinyl, pyrrolidinyltetrazolyl, cyclopentyl, benzyloxy, methyl, dimethylpyrrolidinyl, dioxothiomorpholinyl, trifluoromethyl, methylazetidinyl, ethylpiperidinyl, methoxy, methylamino, amino, diethylamino, hydroxy and ethylbenzimidazolyl.

In an embodiment $R^3$ is (methoxy)(methyl)indolyl, ethylbenzimidazolyl, oxodihydroquinazolinyl, dimethylamino and methylamino.

Specific $R^3$ groups are dimethylamino, phenyl, 4-chlorophenyl, 2-fluorophenyl, 3-fluorophenyl, 4-fluorophenyl, 3,4-difluorophenyl, 2-cyanophenyl, 3-cyanophenyl, 4cyanophenyl, 2-chloro-4-cyanophenyl, 3-cyanofluorophenyl, 3-methoxyphenyl, 4-methoxyphenyl, 2,5-dimethoxyphenyl, 3,4-dimethoxyphenyl, 3-difluoromethoxyphenyl, 4-difluoromethoxyphenyl, 4-carboxyphenyl, 2-nitrophenyl, 3-nitrophenyl, 4-nitrophenyl, 3-fluoro-4-nitrophenyl, 4-acetylaminophenyl, 4 (1-methylpiperazin-4-yl)phenyl, 2-naphthyl, 1-methylpyrrolidin-3-yl, piperidin-1-yl, 1-methylpiperidin-2-yl, 1-methylpiperidin-3-yl, 1-methylpiperidin-4-yl, 1-methylpiperazin-4-yl, azoniabicyclo[2.2.1]heptan-2-yl, 1-pyridin-2-ylpiperidin-3-yl, 2-thienyl, 5-(2-methyl-1,3-thiazol-4-yl)-2-thienyl, 5-[1-methyl-3-trifluoromethyl)-1H-pyrazol-5-yl]-2-thienyl, 5-isoxazol-3-yl-2-thienyl, 5-chloro-2-thienyl, 2-methoxycarbonyl)-3-thienyl, 1,3-thiazol-5-yl, 2,4-dimethyl-1,3-thiazol-5-yl, 2-acetylamino)-4-methyl-1,3-thiazol-5-yl, 1,2-dimethyl-1H-imidazol-4-yl, 1,3,5-trimethyl-1H-pyrazol-4-yl, 3,5-diethylisoxazol-4-yl, 4-methyl-1,2,3-thiadiazol-5-yl, pyridin-3-yl, 2-morpholin-4-ylpyridin-5-yl, 5-methoxy-2-methyl-1H-indol-3-yl, benzothien-3-yl, 2,1,3-benzothiadiazol-5-yl, 2,1,3-benzoxadiazol yl, 2,3-dihydro-1-benzofuran-5-yl, 6,7-dihydro-5H-[1,3]thiazolo[3,2-a]pyrimidin-3-yl, isoquinol-5-yl, 2,3-dihydro-1,4-benzodioxin-6-yl, 4-methyl-3,4-dihydro-2H-1,4-benzoxazin-7-yl, pyridin-4-yl, 4-aminosulfonylphenyl, 2-cyanopyridin-5-yl, 1-isopropylpiperidin-3-yl, 4-methylmorpholin-2-yl, azoniabicyclo[2.2.2]octanyl, morpholin-4-yl, 1H-indol-3-yl, 2-methyl-1H-indol-3-yl, 5-methoxy-1H-indol-3-yl, 5-bromo-1H-indol-3-yl, 5-fluoro-1H-indol-3-yl, 1H-benzimidazol-1-yl, 7-methoxy-1-benzofuran-2-yl, 5-methoxy-1H-indol-2-yl, 5-fluoro-1H-indol-2-yl, [1,2,4]triazolo[1,5-a]pyrimidin-yl, 4-phenyl-1,3-thiazol-2-yl, 5-chloro-1-benzothien-3-yl, 4-chloro-1H-indol-3-yl, 2-oxo-1,3-benzoxazol-3-(2H)-yl, 5-methoxy-2-oxo-2,3-dihydro-1H-indol-3-yl, 6-methoxy-2-oxo-2,3-dihydro-1H-indol-3-yl, 2-ethyl-1H-benzimidazol-1-yl, 1-naphthyl, 2-oxoquinazolin-1-(2H)-yl, 4-methyl-1-oxophthalazin-2-(1H)-yl, 2,4-dichlorophenyl, 2-fluoro-6-(trifluoromethyl)phenyl, 2,6-dichlorophenyl, 2-fluoro-3-(trifluoromethyl)phenyl, 2-methyl-1H-benzimidazol-1-yl, 2-(trifluoromethyl)-1H-benzimidazol-1-yl, 1H-indazol-1-yl, quinolin-3-yl, 1,2-benzisoxazol-3-yl, 2-methyl-1H-indol-1-yl, 1H-1,2,3-benzotriazol-1-yl, 5-cyano-1H-indol-1-yl, 2,3,4,9-tetrahydro-1H-beta-carbolin-4-yl, tert-butoxy, 2,3-dihydro-1H-isoindol-2-yl, 1,2,3,4-tetrahydro-1,8-naphthyridin-5-yl, 5-pyrrolidin-1-yl-2H-tetrazol-2-yl, cyclopentyl, benzyloxy, methyl, 1,3-dimethylpyrrolidin-3-yl, 1,1-dioxothiomorpholin yl, trifluoromethyl, 1-methylazetidin-3-yl, 1-ethylpiperidin-3-yl, methoxy, methylamino, amino, diethylamino, 5-cyano-1H-indol-3-yl, hydroxy and 2-ethyl-1H-3,1-benzimidazol-3-yl.

In an embodiment $R^3$ is 5-methoxy-2-methyl-1H-indol-3-yl, 2-ethyl-1H-3,1-benzimidazol-3-yl, 2-oxoquinazolin-1-2H)-yl, dimethylamino and methylamino.

$R^4$ is preferably hydrogen.

$R^5$ is preferably $C_{1-6}$alkyl, especially methyl. A further preferred $R^5$ group is hydrogen.

Preferably, $R^6$ and $R^8$ are independently hydrogen, $C_{1-6}$alkyl or an optionally substituted 5 or 6 membered saturated or partially saturated heterocycle containing 1, 2 or 3 heteroatoms independently selected from N, O and S; or $R^6$ and $R^8$ together form an oxo group.

More particularly, $R^6$ is hydrogen, $C_{1-4}$alkyl or morpholinyl and $R^8$ is hydrogen or $C_{1-4}$alkyl; or $R^6$ and $R^8$ together form an oxo group.

Specifically, $R^6$ is hydrogen, methyl or morpholin 4-yl and $R^8$ is hydrogen or methyl; or $R^6$ and $R^8$ together form an oxo group.

In one embodiment, $R^6$ is hydrogen, $C_{1-6}$alkyl or a 5 or 6 membered saturated or partially saturated heterocycle containing 1, 2 or 3 heteroatoms independently selected from N, O or S, optionally substituted by $C_{1-6}$alkyl.

Particular $R^6$ groups include hydrogen, methyl and morpholinyl. Most preferably $R^6$ is hydrogen, methyl or morpholin-4-yl.

In one embodiment $R^6$ is hydrogen.

$R^8$ is preferably hydrogen or $C_{1-6}$alkyl. More particularly, $R^8$ is hydrogen or methyl.

In one embodiment $R^8$ is hydrogen.

In an embodiment, $R^6$ and $R^8$ together form an oxo group.

In an embodiment, $R^6$ and $R^8$ are independently selected from hydrogen and $C_{1-6}$alkyl, preferably hydrogen and methyl.

$R^7$ is preferably hydrogen or methyl, especially hydrogen.

In an embodiment $R^9$ is hydroxy, $C_{1-6}$alkyl, halo$C_{1-6}$alkyl or $C_{1-6}$alkoxy.

In another embodiment $R^9$ is hydroxy, halo$C_{1-6}$alkyl or $C_{1-6}$alkoxy.

In another embodiment $R^9$ is hydrogen, $C_{1-6}$alkyl or halo$C_{1-6}$alkyl.

Particular $R^9$ groups include hydrogen, methyl, hydroxy, ethyl, isopropyl, methoxy, propyl, butyl and ethoxy.

In an embodiment $R^9$ is methyl, hydroxy, ethyl, isopropyl, methoxy, propyl, butyl and ethoxy.

Preferably, $R^{10}$ is an optionally substituted ring selected from phenyl, benzyl, thienyl, thiazolyl, thiadiazolyl and pyridinyl.

Preferably $R^{10}$ is unsubstituted or substituted by one, two or three independently selected groups. More particularly, the $R^{10}$ is unsubstituted or monosubstituted.

Preferred optional substituents on the $R^{10}$ are independently selected from amino, hydroxy and oxido. More particularly, the optional substituents are independently selected from amino and oxido.

Particular $R^{10}$ groups include aminophenyl, phenyl, benzyl, thiazolyl, thiadiazolyl, thienyl, aminophenyl and oxidopyridinyl.

In an embodiment $R^{10}$ is thienyl, aminophenyl or oxidopyridinyl.

Preferably, the α1 carbon asymmetric center of the compounds of the present invention has the stereochemical configuration of S. In one embodiment the α1 carbon asymmetric center has the stereochemical configuration of R.

In an embodiment is provided compounds of formula II:

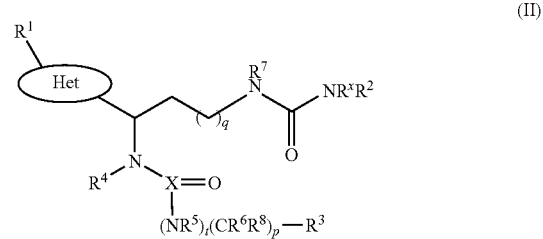

(II)

wherein $R^1$, $R^2$, $R^3$, $R^4$, $R^5$, $R^6$, $R^7$, $R^8$, $R^x$, X, Het, p, q and t are as defined above, or a pharmaceutical acceptable salts, stereoisomer and tautomers thereof. The preferred identities with reference to formula II are as defined previously mutatis mutandis.

The present invention also provides compounds of formula III:

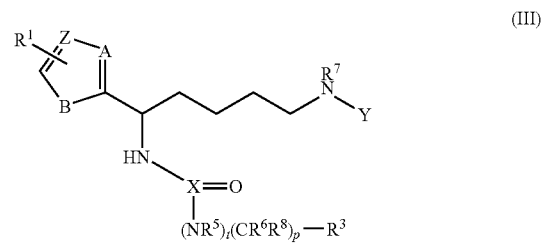

(III)

wherein:
$R^1$, $R^3$, $R^5$, $R^6$, $R^7$, $R^8$, X, Y, p and t are as defined above;
A represents CH or N;
B represents $NR^f$, O or S;
Z represents N or $CR^g$;
$R^f$ represents hydrogen or $C_{1-6}$alkyl; and
$R^g$ represents hydrogen, $C_{1-6}$alkyl or $C_{6-10}$aryl optionally substituted by up to two groups selected from halogen, cyano, $C_{1-6}$alkyl, $C_{1-6}$alkoxy, halo$C_{1-6}$alkyl or halo$C_{1-6}$alkoxy;
or a pharmaceutically acceptable salt, stereoisomer or tautomer thereof A favoured class of compounds of the present invention have the stereochemical configuration of formula IV:

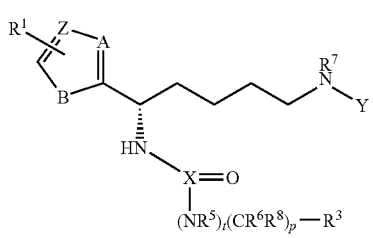

(IV)

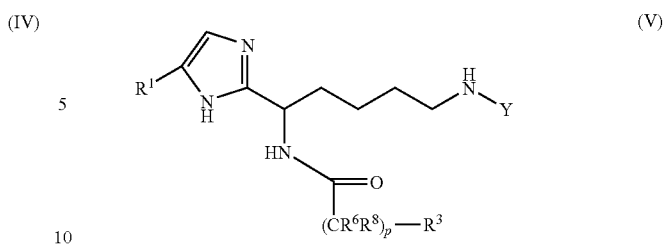

(V)

wherein $R^1$, $R^3$, $R^5$, $R^6$, $R^7$, $R^8$, A, B, x, Y, Z, p and t are as defined above.

The preferred identities with reference to formula III and IV are as defined previously mutatis mutandis.

For the avoidance of doubt, $R^1$ may be attached to any substitutable position of the ring.

In an embodiment Y is $(C=O)NR^xR^2$.

In an embodiment B is $NR^f$ or S.

In one embodiment A is N, B is $NR^f$ or O and Z is N or CR.

In another embodiment A is N, B is $NR^f$ and Z is $CR^g$.

In yet another embodiment A is CH, B is S and Z is $CR^g$.

In another embodiment A and Z are both N and B is $NR^f$.

In an embodiment A is CH, B is $NR^f$ or S and Z is N.

In yet another embodiment B is O.

$R^1$ is preferably phenyl, naphthyl, thienyl, isoxazolyl, pyridinyl, benzothienyl, thiazolotriazolyl, dihydrobenzodioxinyl, benzothiazolyl, quinolinyl or isoquinolinyl, optionally substituted by one or two groups independently selected from cyano, bromine, chlorine, fluorine, methyl, trifluoromethyl, methoxy, difluoromethoxy or phenyl.

$R^3$ is preferably dimethylamino, phenyl, naphthyl, pyrrolidinyl, piperidyl, azoniabicyclo[2.2.1]heptanyl, azoniabicyclo[2.2.2]octanyl, piperazinyl, morpholinyl, thienyl, thiazolyl, imidazolyl, pyrazolyl, isoxazolyl, thiadiazolyl, pyridinyl, indolyl, benzothienyl, benzothiadiazolyl, benzoxadiazolyl, dihydrobenzofuryl, dihydrothiazolopyrimidinyl, isoquinolyl, dihydrobenzodioxinyl, dihydrobenzoxazinyl, tert-butoxy, cyclopentyl, methyl, trifluoromethyl, methoxy, methylamino, amino, diethylamino, hydroxy, benzimidazolyl, benzofuranyl, triazolopyrimidinyl, dihydrobenzoxazolyl, dihydroindolyl, dihydroquinazolinyl, dihydrophthalazinyl, indazolyl, quinolinyl, benzisoxazolyl, benzotriazolyl, tetrahydrobetacarbolinyl, dihydroisoindolyl, tetrahydronaphthyridinyl, tetrazolyl, benzyloxy, thiomorpholinyl and azetidinyl, any of which rings being optionally substituted by one, two or three groups independently selected from chlorine, fluorine, methyl, isopropyl, cyano, methoxy, difluoromethoxy, carboxy, nitro, aminosulfonyl, acetylamino, methylpiperazinyl, pyridinyl, methylthiazolyl, (methyl)(trifluoromethyl)pyrazolyl, isoxazolyl, methoxycarbonyl, morpholinyl, bromo, phenyl, oxo, ethyl, trifluoromethyl and pyrrolidinyl.

$R^5$ is preferably methyl. A further preferred $R^5$ group is hydrogen.

Preferably, $R^6$ and $R^8$ are independently selected from hydrogen and methyl.

$R^f$ is preferably hydrogen or methyl. More particularly $R^f$ is hydrogen.

$R^g$ is preferably hydrogen, $C_{1-6}$alkyl or $C_{6-10}$aryl. More particularly $R^g$ is hydrogen, methyl, phenyl or naphthyl.

In an embodiment $R^g$ is hydrogen.

The present invention also provides compounds represented by formula V:

wherein $R^1$, $R^3$, $R^6$, $R^8$, Y and p are as defined above; or a pharmaceutically acceptable salt, stereoisomer or tautomer thereof.

The preferred identities with reference to formula V are as defined previously mutatis mutandis.

The present invention also includes within its scope N-oxides of the compounds of formula I above. In general, such N-oxides may be formed on any available nitrogen atom. It will be apparent that the N-oxide of a compound of formula I will occur as a zwitterion, wherein an oxido group is attached to an N atom bearing a positive charge. The N-oxides may be formed by conventional means, such as reacting the compound of formula I with oxone in the presence of wet alumina.

In an embodiment of the present invention is provided N-oxides of compounds of formula I wherein $R^{10}$ is 2-oxidopyridin-2-ium.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted The compounds may exist in different isomeric forms, all of which are encompassed by the present invention.

When any variable (e.g. $R^5$ and $R^6$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the aryl as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_1$-$C_6$ alkyl" is defined to include groups having 1, 2, 3, 4, 5 or 6 carbons in a linear or branched arrangement. For example, "$C_1$-$C_6$ alkyl" specifically includes methyl, ethyl, n-propyl, i-propyl, n-butyl, t-butyl, i-butyl, pentyl, hexyl, and so on. The preferred alkyl group is methyl. The term "cycloalkyl" means a monocyclic, bicyclic or polycyclic saturated aliphatic hydrocarbon group having the specified number of carbon atoms. For example, "$C_{7-10}$cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

"Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy group is methoxy.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

The term "hydroxy$C_{1-6}$alkyl" means a $C_1$alkyl group in which one or more (in particular, 1 to 3) hydrogen atoms have been replaced by hydroxy groups. Preferred are $CH_2OH$, $CH_2CHOH$ and $CHOHCH_3$.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present Alkenyl groups include ethenyl propenyl, butenyl and 2-methylbutenyl. The straight or branched portion of the alkenyl group may contain double bonds and may be substituted if a substituted alkenyl group is indicated. Preferred alkenyl groups include ethenyl and propenyl.

The term "$C_{2-6}$alkynyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. The straight or branched portion of the alkynyl group may contain triple bonds and may be substituted if a substituted alkynyl group is indicated. Preferred alkynyl groups include ethynyl and propynyl.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

Examples of particular heterocycles of this invention are benzimidazolyl benzofurandionyl, benzofuranyl benzofuranzanyl, benzopyrazolyl, benzotriazolyl, benzothienyl, benzoxazolyl, benzoxazolonyl, benzothiazolyl, benzothiadiazolyl benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furanyl, furazanyl imidazolyl, indolinyl, indolyl, indolizinyl indolinyl, isoindolinyl, indazolyl, isobenzofuranyl, isoindolyl, isoquinolyl isothiazolyl, isoxazolyl, naphthpyridinyl oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl pyrrolyl, quinazolinyl, quinolyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolidinyl, thiazolyl, thienyl, triazolyl, azetidinyl, 1,4dioxanyl, hexahydroazepinyl, piperazinyl, piperidyl, pyridin-2-onyl, pyrrolidinyl imidazolinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydroisochromenyl, dihydroimidazolonyl, dihydrotriazolonyl, dihydrobenzodioxinyl, dihydrothiazolopyrimidinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl and N-oxides thereof. Further particular heterocycles include dihydroquinazolinyl, dihydrophthalazinyl, dihydroisoindolyl, tetrahydronaphthyridinyl, tetrahydrobetacarbolinyl and N-oxides thereof. Attachment of a heterocyclyl substituent can occur via a carbon atom or via a heteroatom.

A preferred 4 membered saturated heterocycle is azetidinyl.

Preferred 5 or 6 membered saturated or partially saturated heterocycles are pyrrolidinyl, piperidyl, piperazinyl, morpholinyl, azoniabicyclo[2.2.1]heptanyl, azoniabicyclo[2.2.2]octanyl, thiomorpholinyl and thiazolidinyl.

Preferred 5 membered unsaturated heterocycles are thienyl, thiazolyl, pyrazolyl, isoxazolyl, imidazolyl, thiadiazolyl, oxazolyl, triazolyl, tetrazolyl, furyl and oxadiazolyl.

A preferred 6 membered unsaturated heterocycle is pyridinyl.

Preferred 8-10 membered saturated, partially saturated or unsaturated heterocycles are benzothienyl, isoquinolyl, indolyl, benzothiadiazolyl, benzoxadiazolyl, thiazolotriazolyl, dihydrobenzodioxinyl, dihydrothiazolopyrimidinyl, dihydrobenzoxazinyl, dihydrobenzofuranyl, benzothiazolyl, quinolinyl, isoquinolinyl, benzimidazolyl, benzofuranyl, dihydrobenzoxazolyl, dihydroindolyl, dihydroquinazolinyl, dihydrophthalazinyl, indazolyl, benzisoxazolyl, benzotriazolyl, dihydroisoindolyl, tetrahydronaphthyridinyl, triazolopyrimidinyl and tetrahydroquinoliny.

A preferred 13 membered partially saturated heterocycle is tetrahydrobetacarbolinyl.

As used herein, the term 'halogen' refers to fluorine, chlorine, bromine and iodine, of which fluorine, chlorine and bromine are preferred.

Particular compounds within the scope of the present invention include:

2-(1S)-1-{[(5-methoxy-2-methyl-1H-indol-3-yl)acetyl]amino}-5-{[(methylamino)carbonyl]amino}pentyl)-5-(2-naphthyl)-1H-imidazol-3-ium trifluoroacetate;

2-(1S)-1-{[3-(dimethylammonio)propanoyl]amino}-5-{[(methylamino)carbonyl]amino}pentyl)-5-(2-naphthyl)-1H-imidazol-3-ium bis(trifluoroacetate);

2-(1S)-5-{[(hydroxyamino)carbonyl]amino}-1-{[(5-methoxy-2-methyl-1H-indol-3-yl)acetyl]amino}pentyl)-5-(2-naphthyl)-1H-imidazol-3-ium trifluoroacetate;

2-{(1S)-1-{[(5-methoxy-2-methyl-1H-indol-3-yl)acetyl]amino}-5-[(1-oxidopyridin-2-yl)amino]pentyl}-5-(2-naphthyl)-1H-imidazol-3-ium bis(trifluoroacetate);

N-{(1S)-5-amino-1-[5-(2-naphthyl)-1H-imidazol-2-yl]pentyl}-2-(5-methoxy-2-methyl-1H-indol-3-yl)acetamide;

2-{(1S)-1-{[(5-methoxy-2-methyl-1H-indol-3-yl)acetyl]amino}-5-[(2-thienylcarbonyl)amino]pentyl}-5-(2-naphthyl)-1H-imidazol-3-ium trifluoroacetate;

2-(1S)-5-[(2-ammoniobenzoyl)amino]-1-{[(5-methoxy-2-methyl-1H-indol-3-yl)acetyl]amino}pentyl)-5-(2-naphthyl)-1H-imidazol-3-ium;

2-((1S)-5-[(methoxycarbonyl)amino]-1-{[(5-methoxy-2-methyl-1H-indol-3-yl)acetyl]amino}pentyl)-5-(2-naphthyl)-1H-imidazol-3-ium trifluoroacetate;

2-((1S)-1-{[(5-methoxy-2-methyl-1H-indol-3-yl)acetyl]amino}-5-{[(methylamino)carbonothioyl]amino}pentyl)-5-(2-naphthyl)-1H-imidazol-3-ium trifluoroacetate;

2-(1S)-5-{[(2-ammoniophenyl)amino]carbonyl}amino)-1-{[(5-methoxy-2-methyl-1H-indol-3-yl)acetyl]amino}pentyl)-5-(2-naphthyl)-1H-imidazol-3-ium bis(trifluoroacetate);

2-(1S)-1-{[(5-methoxy-2-methyl-1H-indol-3-yl)acetyl]amino}-5-{[(propylamino)carbonyl]amino}pentyl)-5-(2-naphthyl)-1H-imidazol-3-ium trifluoroacetate;

2-(1S)-5-{[(butylamino)carbonyl]amino}-1-{[(5-methoxy-2-methyl-1H-indol-3-yl)acetyl]amino}pentyl}-5-(2-naphthyl)-1H-imidazol-3-ium trifluoroacetate;

2-(1S)-5-{[(ethylamino)carbonyl]amino}-1-{[(5-methoxy-2-methyl-1H-indol-3-yl)acetyl]amino}pentyl)-5-(2-naphthyl)-1H-imidazol-3-ium trifluoroacetate;

2-ethyl-1-[3-({(1S)-5-{[(methylamino)carbonyl]amino}-1-[5-(2-naphthyl)-1H-imidazol-3-ium-2-yl]pentyl}amino)-3-oxopropyl]-1H-3,1-benzimidazol-3-ium bis(trifluoroacetate);

2-(1S)-5-{[(methylamino)carbonyl]amino}-1-{[(2-oxoquinazolin-1-(2H)-yl)acetyl]amino}pentyl)-5-(2-naphthyl)-1H-imidazol-3-ium trifluoroacetate;

2-(1S)-5-{[(methylamino)carbonyl]amino}-1-{[2-methyl-2-(methylammonio)propanoyl]amino}pentyl)-5-(2-naphthyl)-1H-imidazol-3-ium bis(trifluoroacetate);

2-(1S)-5-[(aminocarbonyl)amino]-1-{[(5-methoxy-2-methyl-1H-indol-3-yl)acetyl]amino}pentyl)-5-(2-naphthyl)-1H-imidazol-3-ium trifluoroacetate;

2-(1S)-5-{[(methoxyamino)carbonyl]amino}-1-{[(5-methoxy-2-methyl-1H-indol-3-yl)acetyl]amino}pentyl)-5-(2-naphthyl)-1H-imidazol-3-ium trifluoroacetate;

2-((1S)-{[(ethoxyamino)carbonyl]amino}-1-{[(5-methoxy-2-methyl-1H-indol-3-yl)acetyl]amino}pentyl)-5-(2-naphthyl)-1H-imidazol-3-ium trifluoroacetate;

and the pharmaceutically acceptable bases, salts and stereoisomers thereof.

Included in the instant invention is the free base of compounds of Formula I, as well as the pharmaceutically acceptable salts and stereoisomers thereof. Some of the specific compounds exemplified herein are the protonated salts of amine compounds. Compounds of Formula I containing I or more N atoms may be protonated on any one, some or all of the N atoms. For example, when $R^3$ or the substituent on the $R^{10}$ ring is $N(R^c)_2$, the nitrogen atom may be protonated to form $^+NH(R^c)_2$. Particular protonated $R^3$ groups are methylammonio, dimethylammonio and an optionally substituted benzimidazolium. A particular protonated substitutent on the $R^{10}$ ring is ammonio. When an imidazole ring is present, for example at Het, the ring may be protonated to form imidazolium. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically-acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The compounds of the invention find use in a variety of applications for human and animal health. The compounds of the invention are histone deacetylase (HDAC) inhibitors useful in the treatment of cancer among other diseases. HDACs catalyse the removal of acetyl groups from lysine residues on proteins, including histones and HDAC inhibitors show diverse biological functions including affecting gene expression, cell differentiation, cell cycle progression, growth arrest, and/or apoptosis. See *J. Med. Chem.* 2003, 46:5097 and *Curr. Med. Chem.* 2003, 10:2343.

The compounds of the invention are used to treat cellular proliferation diseases. Disease states which can be treated by the methods and compositions provided herein include, but are not limited to, cancer (further discussed below), neurodegenerative diseases, schizophrenia and stroke. Further diseases include restenosis, mental retardation, inflammatory diseases, immune disorders, diabetes, cardiovascular disorders and asthma.

The compounds, compositions and methods provided herein are particularly deemed useful for the treatment of cancer including solid tumors such as skin, breast, brain, cervical carcinomas, testicular carcinomas, etc. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecolopical: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Further Gastrointestinal cancers which can be treated include colon, colorectal and rectal. Thus, the term "cancerous cell" as provided herein, includes a cell afflicted by any one of the above-identified conditions.

Thus, the present invention provides a compound of formula I for use in the manufacture of a medicament for treating cellular proliferation diseases.

The present invention also provides a method for the treatment of cellular proliferation diseases, which method comprises administration to a patient in need thereof of an effective amount of a compound of formula I or a composition comprising a compound of formula I.

The compounds of the instant invention may also be useful in the treatment or prevention of neurodegenerative diseases, including, but not limited to, polyglutamine-expansion-related neurodegeneration, Huntington's disease, Kennedy's disease, spinocerebellar ataxia, dentatorubralpallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS). See WO 02/090534 and WO 03/083067.

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the invention may also be useful in the treatment or prevention of mental retardation, in particular "X chromosome-linked mental retardation" and "Rubinstein-Taybi syndrome".

Thus, the present invention provides a compound of formula I for the manufacture of a medicament for treating or preventing mental retardation.

The present invention also provides a method for treating or preventing mental retardation, which method comprises administration to a patient in need thereof of an effective amount of a compound of formula I or a composition comprising a compound of formula I.

The compounds of the invention may also be useful in the treatment or prevention of schizophrenia, see WO 02/090534.

Thus, the present invention provides a compound of formula I for the manufacture of a medicament for treating or preventing schizophrenia.

The present invention also provides a method for treating or preventing schizophrenia, which method comprises administration to a patient in need thereof of an effective amount of a compound of formula I or a composition comprising a compound of formula I.

The compounds of the invention may also be useful in the treatment or prevention of inflammatory diseases, including, but not limited to stroke, rheumatoid arthritis, lupus erythematosus, ulcerative colitis and traumatic brain injuries. See Leoni et al., *PNAS*, 99(5):2995-3000 (2002), Suuronen et al., *J. Neurochem*. 87:407-416 (2003) and *Drug Discovery Today*, 10: 197-204 (2005).

Thus, the present invention provides a compound of formula I for the manufacture of a medicament for treating or preventing inflammatory diseases.

The present invention also provides a method for treating or preventing inflamatory diseases, which method comprises administration to a patient in need thereof of an effective amount of a compound of formula I or a composition comprising a compound of formula I.

The compounds of the present invention are also useful in the inhibition of smooth muscle cell proliferation and/or migration and are thus useful in the prevention and/or treatment of restenosis, for example after angioplasty and/or stent implantation.

Thus, the present invention provides a compound of formula I for the manufacture of a medicament for treating or preventing restenosis.

The present invention also provides a method for treating or prevention restenosis, which method comprises administration to a patient in need thereof of an effective amount of a compound of formula I or a composition comprising a compound of formula I.

In one embodiment, smooth muscle cell proliferation and/or migration is inhibited and restenosis is prevented and/or treated by providing a stent device having one or more of the compounds of the instant invention in or on the stent device, e.g. coated onto the stent device. The stent device is designed to controllably release the compounds of the invention, thereby inhibiting smooth miscle cell proliferation and/or migration and preventing and/or treating restenosis.

Stenosis and restenosis are conditions associated with a narrowing of blood vessels. Stenosis of blood vessels generally occurs gradually over time. Restenosis, in contrast, relates to a narrowing of blood vessels following an endovascular procedure, such as balloon angioplasty and/or stent implantation, or a vascular injury.

Balloon angioplasty is typically performed to open a stenotic blood vessel; stenting is usually performed to maintain the patency of a blood vessel after, or in combination with, balloon angioplasty. A stenotic blood vessel is opened with balloon angioplasty by navigating a balloon-tipped catheter to the site of stenosis, and expanding the balloon tip effectively to dilate the occluded blood vessel. In an effort to maintain the patency of the dilated blood vessel, a stent may be implanted in the blood vessel to provide intravascular support to the opened section of the blood vessel, thereby limiting the extent to which the blood vessel will return to its occluded state after release of the balloon catheter. Restenosis is typically caused by trauma inflicted during angioplasty, effected by, for example, balloon dilation, atherectomy or laser ablation treatment of the artery. For these procedures, restenosis occurs at a rate of about 30% to about 60% depending on the vessel location, lesion length and a number of other variables. This reduces the overall success of the relatively non-invasive balloon angioplasty and stenting procedures Restenosis is attributed to many factors, including proliferation of smooth muscle cells (SMC). SMC proliferation is triggered by the initial mechanical injury to the intima that is sustained at the time of balloon angioplasty and stent implantation. The process is characterized by early platelet activation and thrombus formation, followed by SMC recruitment and migration, and, finally, cellular proliferation and extracellular matrix accumulation. Damaged endothelial cells, SMCs, platelets, and macrophages secrete cytokines and growth factors which promote restenosis. SMC proliferation represents the final common pathway leading to neointimal hyperplasia. Therefore, anti-proliferative therapies aimed at inhibiting specific regulatory events in the cell cycle may constitute the most reasonable approach to restenosis after angioplasty.

The compounds of the invention may also be used as immunosuppressants or immunomodulators and can accordingly be used in the treatment or prevention of immune response or immune-mediated responses and diseases such as systemic lupus erythematosus (SLE) and acute or chronic transplant rejection in a recipient of an organ, tissue or cell transplant, (see WO 05/013958).

Examples of autoimmune diseases for which the compounds of the invention may be employed include autoimmune hematological disorders (including hemolytic anaemia, aplastic anaemia, pure red cell anaemia and idiopathic thrombocytopenia), systemic lupus erythematosus, thyroiditis, Hashimoto's thyroiditis, polychondritis, sclerodoma, Wegener granulamatosis, dermatomyositis, chronic active hepatitis, myasthenia gravis, psoriasis, atopic dermatitis, vasculitis, Steven-Johnson syndrome, idiopathic sprue, autoimmune inflammatory bowel disease (including ulcerative colitis and Crohn's disease) endocrine opthalmopathy, Graves disease, sarcoidosis, multiple sclerosis, primary billiary cirrhosis, juvenile diabetes (diabetes mellitus type I), diabetes type II and the disorders associated therewith, uveitis (anterior and posterior), keratoconjunctivitis sicca and vernal keratoconjunctivitis, interstitial lung fibrosis, psoriatic arthritis, glomerulonephritis (with and without nephrotic syndrome, including idiopathic nephrotic syndrome or minimal change nephropathy), juvenile dermatomyositisinfectious, auto-antibody mediated diseases, aplastic anemia, Evan's syndrome, autoimmune hemolytic anemia, infectious diseases causing aberrant immune response and/or activation, such as traumatic or pathogen induced immune disregulation, including for example, that which are caused by hepatitis B and C infections, *staphylococcus aureus* infection, viral encephalitis, sepsis, parasitic diseases wherein damage is induced by inflammatory response (e.g. leprosy); and circulatory diseases, such as arteriosclerosis, atherosclerosis, polyarteritis nodosa and myocarditis.

Thus, the present invention provides a compound of formula I for the manufacture of a medicament for the treatment or prevention of immune disorders.

The present invention also provides a method for treating or preventing immune disorders, which method comprises administration to a patent in need thereof of an effective amount of a compound of formula I or a composition comprising a compound of formula I.

The compounds of the invention may also be useful in the treatment or prevention of other diseases such as diabetes, cardiovascular disorders and asthma The compounds of the invention may also be useful in the treatment or prevention of cardiac hypertrophy and heart failure, as described in *Cell,* 110:479-488 (2002).

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration generally occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. Thus, this invention provides combinations of compounds of formula (I) and known therapeutic agents and/or anti-cancer agents for simultaneous, separate or sequential administration. For example, instant compounds are useful in combination with known anticancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincoft Williams & Wilkins Publishers. A person of ordinary skill in the art would be able to discern which combinations of agents would be useful based on the particular characteristics of the drugs and the cancer involved. Such anti-cancer agents include, but are not limited to, the following: other HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: other HDAC inhibitors, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Examples of "other HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-6s-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-hexane-1,6-diamine)-mu-[diamine-platinum (I)]bis[diamine(chloro)platinum (II)]tetrachloride, diarizidinylspermine, arsenic trioxide, 1-(11-dodecylamino-10-hydroxyundecyl)-3,7-ditnethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazanine.

Examples of proteasome inhibitors include but are not limited to lactacystin, bortezomib, epoxomicin and peptide aldehydes such as MG 132, MG 115 and PSI. A further inhibitor is MLN-341 (Velcade).

In an embodiment, the compounds of the present invention may be used in combination with other HDAC inhibitors such as SAHA and proteasome inhibitors.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylwnide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-d]acridin-6-one, N-[1-[2(diethylamino) ethylamino]-7-methoxy-9-oxo-9H-thioxanthen-4-ylmethyl] formamide, N-(2-dimethylamino)ethyl)acridine-4-carboxamide, 6-[[2-(dimethylamino)ethyl]amino]-3-hydroxy-7H-indeno[2,1-c]quinolin 7-one, and dimesna.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. Further examples of inhibitors are described in WO04/126699, WO05/018638, WO05/019206, WO05/019205, WO05/018547, WO05/017190 and US2005/0176776. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofirin, decitabine, nolatrexed, pemetrexed, neizarabine, 2'-deoxy-2'-methylidenecytidine, 2'-fluoromethylene-2'-deoxycytidine, N-[5-(2,3-dihydrobenzofuryl)sulfonyl]-N'-3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)ethyl]-2,5-thienoyl-L-glutamic acid, aminopterin, 5-fluorouracil, alanosine, 11-acetyl-8-(carbamoyloxymethyl) formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone. A further agent is trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-I (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of EGFR (for example gefitinb and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAYA43-9006), inhibitors of MEK (for example CI-1040 and PD098059) and inhibitors of mTOR (for example Wyeth CCI-779 and Ariad AP23573). Further inhibitors of serine/threonine kinases are those described in US 2004-0116432, US 2004-0102360, WO 03/086279, WO 03/086394, WO 03/084473, WO 2004/041162, WO 2004/096131, WO 04/096129, WO 04/096135, WO 04/096130, WO 05/100356, WO 05/100344, US 2005/029941, US 2005/44294, US 2005/43361, 60/734,188, 60/652,737 and 60/670,469. Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134, 142, 5,380,738, 5,393,790, 5,466,823, 5,633,272, and 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof. A further useful COX-2 inhibitor is 3-phenyl-4-(4-methylsulfonyl)phenyl)-2-(5H)-furanone.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpinase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chlorofluorophenylamino)-7-methoxy-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol. Vis. Sci.* 2000, 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthalmol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-yl)oxy]-2-methylpropionic acid (disclosed in U.S. Ser. No. 09/782,856), and 2-(R)-7-(3-(2-chloro-4-(4 fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet.* 61:785-789, 1997) and Kufe et al (*Cancer Medicine*, 5th Ed, pp 876889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexmethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430

771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia Such an anemia treatment agent is, for example, a continuous eythropoiesis receptor activator (such as epoetin alfa).

A compound of the instant invention may also be administered with an agent useful in the treatment of neutropenia Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleuking); Alemtuuumabb (Campath®); alitretinoin (Panretin®); allopurinol (Zyloprim®); altretamine (Hexylen®); amifostine (Ethyol®); anastrozole (Ammidex®); arsenic trioxide (Trisenox®); asparaginase (Elspar®); azacitidine (Vidaza®); bevacuzimab (Avastin®); bexarotene capsules (Targreting); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®)); clofarabine (Clolar®); cyclophosphamide (Cytoxan®, Neosar®); cyclophosphamide (Cytoxan Injection®)); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrncil®); fulvestrant (Faslodex®); gefitinib (Iressa®); gemcitabine (Gemzar®); gemtuzumab ozogamnicin (Mylotara®); goserelin acetate (Zoladex Implant®); goserelin acetate (Zoladex®); histrelin acetate (Histrelin Implant®); hydroxyurea (Hydrea®); Ibritumomab Tiuxetan (Zevalin®);

idarubicin (Idamycin®); ifosfamide (IFEX®); imatib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-500); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithiacin®); porfimer sodium (Photofriin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6TG (Thioguanine®); thiotepa (Thioplex®); topotecan (Hycamtin®); toremifene (Fareston®); Tositumomab (Bexxar®); Tositumomab/1-131 tositumomab (Bexxar®)); Trastuzunab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an ITV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interferes with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: other HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interferes with a cell cycle checkpoint, an apoptosis inducing agent and a bisphosphonate.

These and other aspects of the invention will be apparent from the teachings contained herein.

All patents, publications and pending patent applications identified are hereby incorporated by reference.

Abbreviations used in the description of the chemistry and in the Examples that follow are: DMF: dimethylformamide; DMSO: dimethylsulfoxide; MeOH: methanol; ETOH: ethanol; EtOAc: ethyl acetate; DCM: dichloromethane; TFA: trifluoroacetic acid; (g): gas; min: minutes; h: hour(s); eq.: equivalent(s); M: molar, RT: room temperature; RP-HPLC: reversed phase high-pressure liquid chromatography; DIPEA: N,N-diisopropylethylamine; EDCI: 1-(3-dimethylaminopropyl)-3-ethylcarbodiimide hydrochloride; HOBt 1-hydroxybenzotriazole; and HATU: O-(7-azabenzotriazol-1-yl)-N,N,N',N'-tetramethyluronium hexafluorophosphate.

Compounds of formula I wherein Y is (C=O)NHR² can be prepared by reacting a compound of formula IA with a compound of formula IB:

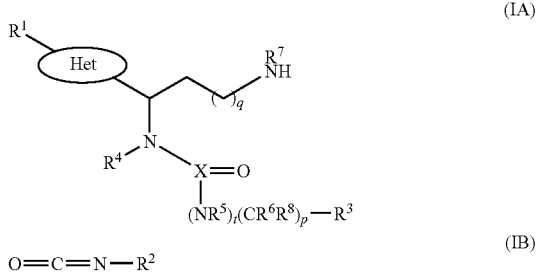

(IA)

O=C=N—R²

(IB)

wherein $R^1$, $R^2$, $R^3$, $R^4$, $R^5$, $R^6$, $R^7$, $R^8$, X, Het, p, q and t are as defined above, generally in the presence of a base such as DIPEA and a solvent such as DMF at about room temperature.

Compounds of formula IA can be prepared from reacting a compound of formula IC and a compound of formula ID:

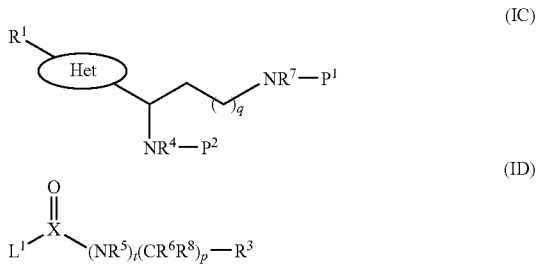

(IC)

(ID)

wherein $R^1$, $R^3$, $R^4$, $R^5$, $R^6$, $R^7$, $R^8$, X, Het, p, q and t are as defined above, $P^1$ is a protecting group such as Cbz (benzyloxycarbonyl), $P^2$ is a protecting group such as Boc (tert-butyloxycarbonyl) and $L^1$ is a leaving group such as hydroxy or halogen. The $P^2$ protecting group such as Boc in the compound of formula IC may be removed prior to this coupling reaction using standard techniques, such as the use of an acid such as TFA in a solvent such as DCM at about 0° C. to room temperature, to produce a trifluoroacetate salt of the compound. When $L^1$ is a leaving group such as halogen, for example chlorine, the reaction is generally carried out in the presence of a base such as Et₃N and a solvent such as DMF or DCM at about room temperature. When $L^1$ is a leaving group such as hydroxy, a coupling agent such as EDC.HCl and a base such as Et₃N may also be added. A further coupling agent such as HOBt and a base such as DIPEA may also be present. A coupling agent such as HATU in the presence of a base such as DIPEA and solvents such as DMF and DCM may also be used.

The $P^2$ protecting group such as Boc may be removed prior to this reaction using standard techniques, such as adding an acid such as TFA in a solvent such as DCM at about 0° C. to room temperature to produce a trifluoroacetate salt of the compound.

Compounds of formula IC wherein Het is imidazole can be prepared by reacting a compound of formula IE:

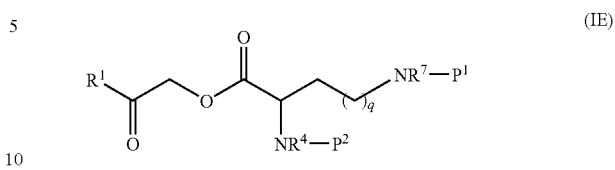

(IE)

wherein $R^1$, $R^4$, $R^7$, q, $P^1$ and $P^2$ are as defined above with a cyclisation agent such as ammonium acetate. The reaction is generally carried out in a solvent such as toluene under reflux, for example using a Dean-Stark trap.

Compounds of formula IE can be prepared by reacting a compound of formula IF with a compound of formula IG;

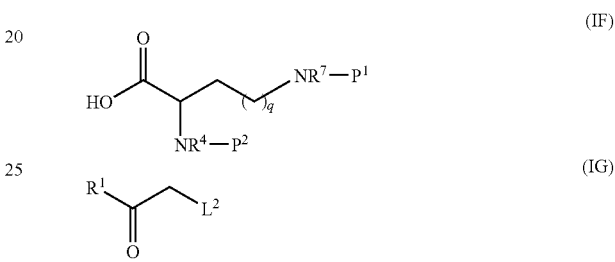

(IF)

(IG)

wherein $R^1$, $R^4$, $R^7$, q, $P^1$ and $P^2$ are as defined above and $L^2$ is a leaving group such as halogen, particularly bromine, generally in the presence of a base such as cesium carbonate in a solvent such as DMF at about room temperature.

Alternatively, compounds of formula I can be prepared from reacting a compound of formula IH:

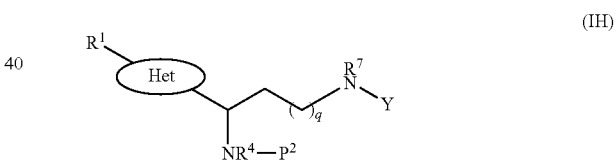

(IH)

wherein $R^1$, $R^4$, $R^7$, Y, Het, q and $P^2$ are as defined above, with a compound of formula D. The $P^2$ protecting group such as Boc in the compound of formula IH can be removed prior to this coupling reaction using standard techniques, such as adding an acid such as TFA in a solvent such as DCM at about 0° C. to room temperature, to produce a trifluoroacetate salt of the compound. The coupling reaction is generally carried out under coupling conditions analogous to those described for the reaction between compounds of formula IC and ID.

Compounds of formula IH wherein Y is (C=O)NHR² can be prepared by reacting a compound of formula IJ:

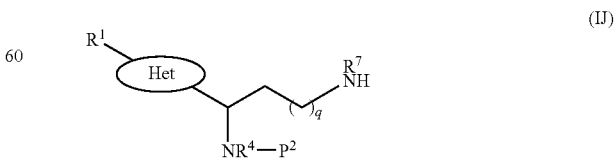

(IJ)

wherein $R^1$, $R^2$, $R^4$, $R^7$, Het, q and $P^2$ are as defined above, with a compound of formula IB. The reaction is generally carried out in the presence of solvents such as DCM and DMF at about 0° C. The reaction condition analogous to those described for the reaction between compounds of formula IA and IB may also be used.

Compounds of formula IJ can be prepared by removing the P¹ protecting group from a compound for formula IK:

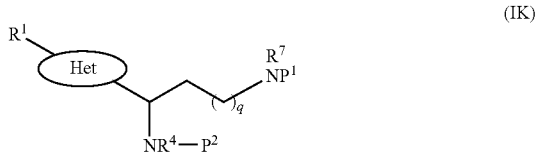

(IK)

wherein R¹, R⁴, R⁷, Het, q, P¹ and P² are as defined above, generally using standard methods such as those described above.

Alternatively, compounds of formula I wherein Y is (C=O)NR$^x$R² or (C=S)NR$^x$R² can be prepared by reacting a compound of formula IA with a carbonylation agent such as triphosgene or a thiocarbonylation agent such as thiophosgene, generally in the presence of a base such as Et₃N, and solvents such as DCM and DMF at about 0° C. to room temperature; followed by reacting with a compound of formula IL, generally at about room temperature:

(IL)

wherein R² and R$^x$ are as defined above.

Alternatively, compounds of formula I can be prepared by reacting a compound of formula IA with a compound of formula IM:

L²—Y (IM)

wherein Y is as defined above and L² is a leaving group such as halogen, for example bromine, in the presence of a base such as sodium hydrocarbonate, a solvent such as 1-butanol, at about 100° C.

Alternatively, compounds of formula I can be prepared by reacting a compound of formula IA with an appropriate Y containing electrophile such as an acid chloride, thioisocyanate or chloroformate, generally in the presence of a base such as DIPEA and a solvent such as DMF at about 0° C. to room temperature.

Where the synthesis of intermediates and starting materials is not described, these compounds are commercially available or can be made from commercially available compounds by standard methods or by extension of the Examples herein.

Compounds of formula I may be converted to other compounds of formula I by known methods or by methods described in the Examples.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. *Protecting Groups*, Thieme, 1994. The protecting groups may be removed at a convenient subsequent stage using methods known from the art. For example, when the Boc protecting group is present, it may be removed by the addition of solvents such as TFA and DCM.

Compounds of this invention can be prepared as described in the following schemes.

Scheme 1

In Scheme 1, synthesis of the imidazole ring was performed by reaction of the Nα-Boc-Nε-Z-L-lysine with α-bromethylarylketones as described in WO 02/10140. Deprotection of the Boc-protected amino group in acidic conditions, as described in *Int. J. Pept. Protein Res.* 1984, 23, 565, was followed by amide coupling using standard procedures as described in *J. Chem. Soc.; Chem. Commun.* 1994, 201, and hydrogenolisis of the Cbz group following the procedure described in *Ber.* 1932, 65, 1192. Introduction of the ZBG (Zinc Binding Group) was accomplished by addition of the corresponding electrophile to the free amino intermediate using methods described in the art as in *Russ. Chem. Rev.* 1985, 54, 249.

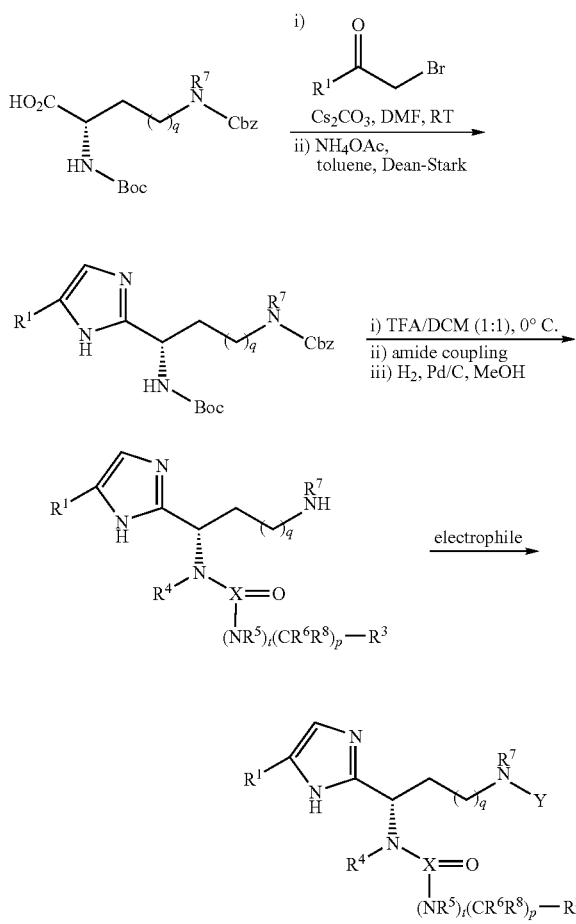

Scheme 2

In Scheme 2, the terminal N-Cbz group of the imidazole intermediate was deprotected and treated with an isocyanate agent. Then, deprotection of the N-Boc group in acidic conditions followed by amide coupling led to the targeted molecules. In all the cases the methodologies mentioned in Scheme 1 were used.

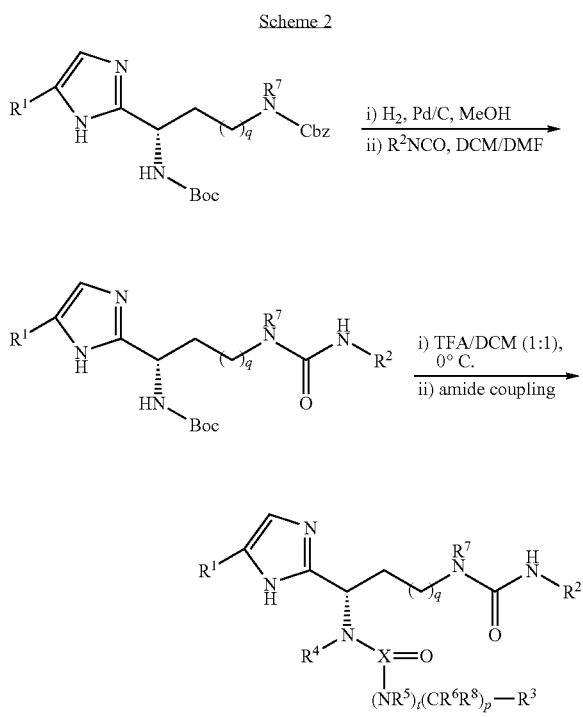

Scheme 3

In Scheme 3, the terminal amino group was functionalized by formation of the isocyanate in the presence of triphosgene. Subsequent addition of the appropriate hydroxylamine or derivative thereof as described in *Chem. Pharm. Bull* 2002, 50, 1280, led to the N-hydroxyurea derivatives

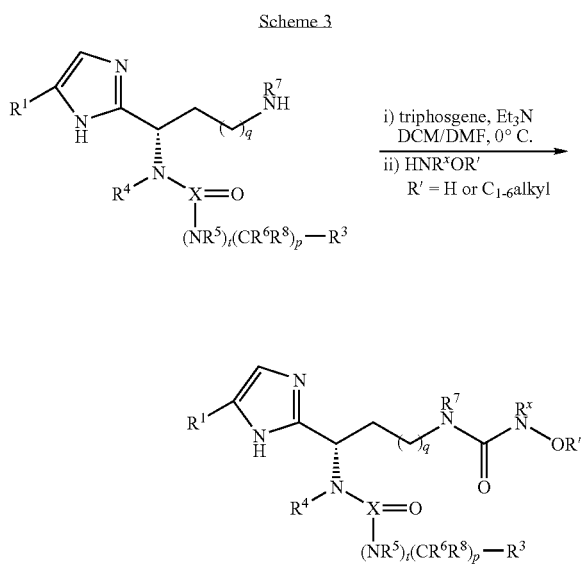

Scheme 4

In Scheme 4, reaction of amino group with an activated 2-haloheterocycle in the presence of a base following the procedure described in *Biorg. Med. Chem. Lett.* 1994, 4, 2165 led to the N-substituted heterocyclic compound.

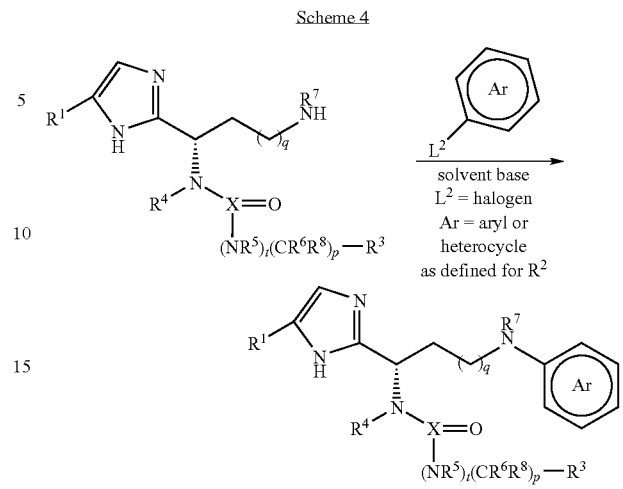

The exemplified compounds described herein were tested by the assays described below and were found to have an $IC_{50}$ value of less than 10 1M.

HDAC1 Assay

Assay Description:

The HDAC1 assay is used to quantify the histone deacetylase (HDAC) activity. The assay is performed in 96 well microtiter plates by pro-incubating serial dilutions of compounds with a fixed concentration of HeLa nuclear extract or purified HDAC1 and then adding an acetylated lysine-containing substrate/developer that fluoresces upon deacetylation. The deacetylase reaction is performed at 37° C. for 60 min, terminated by addition of the developer solution, and then fluorescence (ex 360 nM, em 460 nM) is measured using a plate reader.

HDAC Substrate Buffer System

Reagents of the HDAC Fluorescent Activity Assay are purchased from BioMol Research Laboratories (Plymouth Meeting, Pa.) and feature the Fluor-de-Lys™ Substrate/Developer System. The reagents include the proprietary fluorescent substrate as a 50 mM stock solution (KI-104), and the Developer Concentrate (KI-105). Deacetylation of the lysine residue of the Fluor-de-Lys substrate is quantified by measuring the fluorescence (ex 360 nM, em 460 nM) after addition of the proprietary Developer.

Working Reagents:

TSA Stock: TSA is provided as a 10 mM stock solution in 100% dimethylsulfoxide (DMSO). Assay Buffer: 25 mM Tris/HCl pH8, 137 mM NaCl, 2.7 mM KCl, 1 mM $MgCl_2$, 0.1 mg/ml BSA Diluted Substrate Solution: The commercial 50 mM Fluor-de-Lys substrate (KI-104) is diluted to 150 uM with HDAC Assay Buffer prior to each use. The final concentration in the assay is 30 uM. Diluted Developer Solution: The commercial 20× Developer Concentrate (KI-105) is diluted 1:167 into HDAC Assay Buffer. 2 uM [final] TSA to this solution increases its ability to stop the reaction. HDAC1 Working Solution: The HDAC1 enzyme is diluted in assay buffer prior to each use from a fresh aliquot of enzyme. The final concentration in the assay is 1-2 nM.

Compounds: Test compounds should be prepared as a 10×5% DMSO solution in assay buffer. The final DMSO concentration in the reaction is 0.5%.

Experimental Design:

The reaction is performed in 96-well microplate in a final volume of 50 ul/well, as following:

Add 5 ul of DMSO/compound solution
Add 35 ul of HDAC1 in assay buffer (or 35 ul assay buffer in the negative controls)
Incubate 10' at room temperature
Start the reaction by adding 10 ul of the 150 uM Substrate Solution
Incubate 1 h at 37° C.
Stop by adding 50 ul of Developer/4 uM TSA solution
Incubate 10 min at room temperature
Measure the fluorescence at Ex.360 nM and Em.460 nM Extraction and Purification Protocol for Flag-Tagged HDAC1 Expressed in HeLa Cells HeLa cells transiently transfected with pCDNA3-HDAC1-FLAG are grown to 80% confluence on 10 cm culture dishes in DMEM, 10% Fetal bovine serum supplemented with antibiotics and glutamine. Cells are washed with 10 ml cold PBS and scraped into 2 ml of PBS. Cells are centrifuged for 5 minutes at 800×g at 4° C., washed with 30 ml PBS and resuspended in 10 ml PBS, counted, re-centrifuged and frozen at −80° C.

The frozen cell pellet is re-suspended in 1 ml of hypotonic lysis buffer (LB: 20 mM Hepes pH7.9, 0.25 mM EDTA, 10% glycerol) containing COMPLETE protease inhibitor and incubated on ice for 15 minutes, followed by homogenization on a 2-ml DounceB homogenizer (25 strokes). 150 mM KCl and 0.5% NP-40 are added to the homogenate and the solution is sonicated twice for 30 seconds (output ⅝, duty cycle 90) and incubated for 1 hour at 4° C. After a 30 minutes centrifugation at 12000 rpm and 4° C. the supernatant (soluble extract) is collected and protein concentration is determined using the BIORAD assay.

Anti-FLAG M2 affinity resin (Sigma) is washed three times with TBS and twice with LB. 10 μl of the LB-washed resin/mg of protein (2-3 ug of Flagged-HDAC1) are added to the soluble extract (1 mL) and incubated overnight at 4° C. with gentle mixing. The resin is then collected by centrifugation, washed once with LB, twice with LB+0.1% NP40 and twice with elution buffer (50 mM Hepes pH 7.4, 5% glycerol, 100 mM KCl, 0.01% Triton X-100).

The affinity-purified HDAC is eluted from the resin by addition of a 10-fold excess (with respect to the resin) of elution buffer containing 100 μg/ml 3×FLAG peptide (SIGMA). The concentration of purified HDAC is determined by Western blot analysis.

Other assays are known in the literature and can be readily performed by those skilled in the art.

The following Examples illustrate the present invention.

EXAMPLE 1

2-((1S)-1-{[(5-methoxy-2-methyl-1H-indol-3-yl)acetyl]amino}-5-{[(methylamino)carbonyl]amino}pentyl)-5-(2-naphthyl)-1H-imidazol-3-ium trifluoroacetate Step 1: tert-butyl {(1S)-5-aminobenzyloxycarbonyl-1-[5-(2-naphthyl)-1H-imidazol-2-yl]pentyl}carbamate A solution of $N^6$-[(benzyloxy)carbonyl]-$N^2$-(tert-butoxycarbonyl)-L-lysine and $Cs_2CO_3$ (0.5 eq.) in ETOH was stirred at RT for 90 min. Then, after concentration under reduced pressure the resulting salt was dissolved in DMF. The resulting solution (0.13 M) was treated with 2-bromo-2' acetonaphthone (1 eq.) and the mixture was stirred at RT for 2 h. After removal of the DMF by azeotropic evaporation with toluene, EtOAc was added and the resulting mixture was filtered. The solid was washed with EtOAc and the combined filtrates were concentrated under reduced pressure to give an oil which was dissolved in toluene. Ammonium acetate (20 eq.) was added to the solution (0.1 M) and the mixture was to reflux with a Dean-Stark trap for 2 h and 30 min. After cooling down, the reaction mixture was diluted with EtOAc and washed with $NaHCO_3$ (saturated solution), water and brine, then dried and concentrated to yield (99%) the title compound as a solid.

$^1$H NMR (400 MHz, DMSO-$d_6$, 300K) δ 11.84 (s, 1H), 8.24 (s, 1H), 7.97-7.78 (m, 51), 7.62 (s, 1H), 7.40-7.23 (m, 8H), 4.99 (s, 2H), 4.69-4.52 (m, 1H), 3.04-2.92 (m, 2H), 1.92-1.78 (m, 2H), 1.40 (s, 9H), 1.48-1.20 (m, 4H). MS (ES$^+$) $C_{31}H_{36}N_4O_4$ requires: 528, found. 529 (M+H)$^+$.

Step 2: 2-((1S)-1-ammonio-5-{[(benzyloxy)carbonyl]amino}pentyl)-5-(2-naphthyl)-1H-imidazol-3-ium bis(trifluoroacetate)

The product from step 1 was dissolved in TFA/DCM (1:1) at 0° C. and the resulting solution (0.2 M) was stirred at RT for 2 h. 30 min. Removal of the solvent under reduced pressure yielded (100%) the title compound as a solid.

$^1$H NMR (400 MHz, DMSO$_6$, 300K) δ 8.44 (bs, 3H), 8.28 (s, 1H), 8.02-7.85 (m, 4H), 7.81 (s, 1H), 7.56-7.41 (m, 2H), 7.38-725 (m, 4H), 7.21 (bs, 1H), 4.97 (s, 2H), 4.36 (bs, 1H), 2.98 (m, 2H), 2.07-1.85 (m, 2H) 1.52-1.35 (m, 2H), 1.35-1.15 (m, 2H). MS (ES$^+$) $C_{26}H_{30}N_4O_2$ requires: 428, found. 429 (M+H)$^+$.

Step 3: benzyl {(5S)-5-{[(5-methoxy-2-methyl-1H-indol-3-yl)acetyl]amino}-5-[5-(2-naphthyl)-1H-imidazol-2-yl]pentyl}carbamate To a stirred solution (0.5 M) of the product from step 2 in DMF were added EDCI (1.5 eq.), HOBt (1.5 eq.), (5-methoxy-2-methyl-1H-indol-3-yl)acetic acid (1.5 eq.) and DIPEA (6 eq.) and the reaction mixture was stirred at RT for 16 h. Then, it was diluted with EtOAc and washed with 1N HCl, brine and dried. Evaporation of the solvent under reduced pressure gave a crude that was purified by flash chromatography on silica gel (1:4 to 1:3 EtOAc/petroleum ether) to yield (77%) the title compound as a solid.

$^1$H NMR (400 MHz, DMSO $d_6$, 300K) δ 11.97 (s, 1H), 10.59 (s, 1H), 8.22 (s, 1H), 7.96-7.76 (m, 4H), 7.62 (s, 1H), 7.53-7.38 (m, 2H), 7.37-7.24 (m, 5H), 7.19 (bs, 1H), 7.13-7.05 (m, 1H), 6.63-6.45 (m, 1H), 4.98 (s, 2H), 4.95-4.87 (m, 1H), 3.66 (s, 3H), 3.56-3.43 (m, 2H), 2.96-2.87 (m, 2H), 2.32 (s, 3H), 1.96-1.70 (m, 2H), 1.45-1.34 (m, 2H), 1.35-1.15 (m, 2H). MS (ES$^+$) $C_{39}H_{39}N_5O_4$ requires: 629, found: 630 (M+H)$^+$.

Step 4: N-{(1S)-5-amino-1-[5-(2-naphthyl)-1H-imidazol-2-yl]pentyl}-2-(5-methoxy-2-methyl-1H-indol-3-yl)acetamide A stirred solution (0.2 M) of the product from step 3 in MeOH was added to 10% Pd on carbon (17% w/w) and the heterogeneous mixture was stirred under $H_2$ (g) at RT for the weekend. The reaction mixture was filtered through a pad of celite and washed with MeOH. Evaporation of the solvent yielded (94%) the title compound as a solid.

$^1$H NMR (400 MHz, DMSO-$d_6$, 300K) δ 10.59 (s, 1H), 8.28 (d, J=8.3 Hz, 1H), 8.21 (s, 1H), 7.93-7.81 (m, 4H), 7.59 (s, 1H), 7.52-7.38 (m, 2H), 7.10 (d, J=8.5 Hz, 1H), 7.06-6.98

(m, 1H), 6.59 (d, J=8.5 Hz, 1H), 4.98-4.87 (m, 1H), 3.68 (s, 3H), 3.58-3.47 (m, 2H), 2.44 (d, J=6.3 Hz, 2H) 2.33 (s, 3H), 1.96-1.83 (m, 1H), 1.83-1.70 (m, 1H), 1.43-1.10 (m, 4H). MS (ES$^+$) $C_{30}H_{33}N_5O_2$ requires: 495, found: 496 (M+H)$^+$.

Step 5: 2-(1S)-1-{[(5-methoxy-2-methyl-1H-indol-3-yl)acetyl]amino}-5-{[(methylamino)carbonyl]amino}pentyl)-5-(2-naphthyl)-1H-imidazol-3-ium trifluoroacetate To stirred solution (0.1 M) of the product from step 4 and DIPEA (2 eq.) in DMF, methyl isocyanate (1.1 eq.) was added. The reaction mixture was stirred at RT overnight, then, it was purified by RP-HPLC (Waters Symetry Prep C18, 7 micron, 19×300 mm; flow: 20 mL/min; Gradient: A: H$_2$O+ 0.1% TFA; B: MeCN+0.1% TFA; 70% A isocratic for 2 min, linear to 10% A in 14 min) to yield (36%) the title compound as a solid.

$^1$H NMR (400 MHz, DMSO-d$_6$, 300K) δ 10.62 (s, 1H), 8.59 (bs, 1H), 8.32 (s, 1H), 8.14 (bs, 1H), 8.06 (d, J=8.8 Hz, 1H), 7.96 (t, J=8.8 Hz, 2H), 7.89 (dd, J=8.4 Hz J=1.6 Hz, 1H), 7.62-7.56 (m, 2H), 7.10 (d, J=8.8 Hz, 1H), 6.96 (d, J=2.4 Hz, 1H), 6.60 (dd, J=8.4 Hz J=2.4 Hz, 1H), 5.86 (bs, 1H), 5.66 (bs, 1H), 5.05-4.96 (m, 1H), 3.67 (s, 3H), 3.59 (d, J=11.2 Hz, 1H), 3.51 (d, J=11.2 Hz, 1H), 2.94 (bs, 2H), 2.30 (s, 3H), 2.04-1.87 (m, 2H), 1.43-1.17 (m, 4H). MS (ES$^+$) $C_{32}H_{36}N_6O_3$ requires: 552, found. 553 (M+H)$^+$.

EXAMPLE 2

2-((1S)-1-{[3-(dimethylammonio)propanoyl]amino}-5-{[(methylamino)carbonyl]amino}pentyl)-5-(2-naphthyl)-1H-imidazol-3-ium bis(trifluoroacetate)

Step 1: tert-butyl {(1S)-5-amino-1-[5-(2-naphthyl)-1H-imidazol-2-yl]pentyl}carbamate A stirred solution (0.2 M) of the product from example 1 step 1 in MeOH was added to 10% Pd on carbon (20% w/w) and the heterogeneous mixture was stirred under H$_2$ (g) at RT overnight. Then, the reaction mixture was filtered through a pad of celite and washed with MeOH. Evaporation of the solvent yielded (95%) the title compound as a solid.

$^1$H NMR (400 MHz, DMSO d$_6$, 300K) δ 8.22 (s, 1H), 7.93-7.79 (m, 4H), 7.58 (s, 1H), 7.51-7.37 (m, 2H), 7.12 (d, J=8.3 Hz, 1H), 4.68-4.56 (m, 1H), 1.91-1.79 (m, 2H), 1.48-1.18 (m, 6H), 1.40 (s, 9H). MS (ES$^+$) $C_{23}CH_{30}N_4O_2$ requires: 394, found. 395 (M+H)$^+$.

Step 2: tert-butyl {(1S)-5-{[(methylamino)carbonyl]amino}-1-[5-(2-naphthyl)-1H-imidazol-2-yl]pentyl}carbamate To a stirred solution (0.18 M) of the product from step 1 in DCM/DMF (2:1) at 0° C., methyl isocyanate (1 eq.) was added. The reaction mixture was stirred at 0° C. for 1 h. Then, NaHCO$_3$ (saturated solution) was added and extracted with EtOAc. The combined organic layers were dried. Evaporation of the solvent gave a crude that was purified by flash chromatography on silica gel (95:5 DCM/MeOH) to yield (63%) the title compound as a solid.

$^1$H NMR (400 M1z, DMSO$_6$, 300K) δ 11.84 (1H, s), 8.24 (s, 1H), 7.96-7.78 (s, 4H), 7.61 (s, 1H), 7.52-7.37 (m, 2H), 7.08 (d, J=8.1 Hz, 1H), 5.82 (bs, 1H), 5.62 (bs, 1H), 4.68-4.54 (m, 1H), 3.01-2.99 (m, 2H), 1.92-1.68 (m, 2H), 1.45-1.15 (m, 6H), 1.40 (s, 9H). MS (ES$^+$) $C_{25}H_{33}N_5O_3$ requires: 451, found. 452 (M+H)$^+$.

Step 3: 2-(1S)-1-ammonio-5-{[(methylamino)carbonyl]amino}pentyl)-5-(2-naphthyl)-1H-imidazol-3-ium bis(trifluoroacetate)

The product from step 2 was dissolved in TFA/DCM (1:1) at 0° C. and the resulting solution (0.18 M) was stirred at 0° C. for 3 h. 30 min. Removal of the solvent under reduced pressure yielded (100%) the title compound as a solid.

$^1$H NMR (400 MHz, DMSO$_6$, 300K) δ 8.60 (s, 3H), 8.31 (s, 1H), 7.94 (s, 1H), 8.00-7.87 (m, 4H), 7.58-7.46 (m, 2H), 4.54-4.43 (m, 1H), 2.96 (t, J=7.2 Hz, 2H), 2.03-1.90 (m, 2H), 1.45-1.13 (m, 4H). MS (ES$^+$) $C_{20}H_{25}N_5O$ requires: 351, found: 352 (M+H)$^+$.

Step 4: 2-((1S)-1-{[3-(dimethylammonio)propanoyl]amino}-5-{[(methylamino)carbonyl]amino}pentyl)-5-(2-naphthyl)-1H-imidazol-3-ium bis(trifluoroacetate)

To a stirred solution (0.05 M) of the product from step 3 in DMF/DCM (2:1) were added HATU (1.1 eq.), DIPEA (3 eq.) and 2-carboxy-N,N-dimethylethanaminium chloride (1 eq.) and the reaction mixture was stirred at RT overnight. Then, it was concentrated and purified by RP-HPLC (Waters Symetry Prep C18, 7 micron, 19×300 mm; flow: 20 mL/min; Gradient: A: H$_2$O+0.1% TFA; B: MeCN+0.1% TFA; 80% A isocratic for 2 min, linear to 30% A in 14 min) to yield (26%) the title compound as a colourless oil. $^1$H NMR (400 MHz, DMSO d$_6$, 300K) δ 8.89 (bs, 1H), 833 (s, 1H), 8.12-7.99 (m, 2H), 7.99-7.87 (m, 3H), 7.62-7.51 (m, 2H), 5.89 (bs, 1H), 5.69 (bs, 1H), 5.08-4.97 (m, 1H), 330 (t, J=7.2 Hz, 2H), 2.98 (bs, 2H), 2.77 (s, 6H), 2.76-2.66 (m, 1H), 2.05-1.83 (m, 2H) 1.48-1.20 (m, 4H). MS (ES$^+$) $CH_{34}N_6O_2$ requires: 450, found: 451 (M+H)$^+$.

EXAMPLE 3

2-((1S)-5-{[(hydroxyamino)carbonyl]amino}-1-{[(5-methoxy-2-methyl-1H-indol-3-yl)acetyl]amino}pentyl)-5-(2-naphthyl)-1H-imidazol-3-ium trifluoroacetate To a stirred solution (0.04 M) of the product from example 1 step 4 and Et$_3$N (1 eq.) in DCM/DMF (3:1) at 0° C., triphosgene (0.33 eq.) was added. The reaction mixture was stirred at 0° C. for 1 h., then, O-(tert-butyldimethylsilyl)hydroxylamine (large excess) was added and the resulting reaction mixture was stirred at RT overnight. After addition of TFA/water (1:1) and stirring of the mixture for another 4 h, the solvent was concentrated to give a crude product which was purified by RP-HPLC (Waters Symetry Prep C18, 7 micron, 19×300 mm; flow: 20 mL/min; Gradient: A: H$_2$O+ 0.1% TFA; B: MeCN+0.1% TFA; 80% A isocratic for 2 min, linear to 20% A in 14 min) to yield (40%) the title compound as a solid. $^1$H NMR (400 MHz, DMSO-d$_6$, 300K) δ $^1$H NMR (400 MHz, DMSO d$_6$, 300K) δ 10.61 (s, 1H), 8.60 (bs, 1H), 8.51 (bs, 1H), 8.33 (s, 1H), 8.25 (bs, 1H), 8.07 (d, J=9.2 Hz, 1H), 7.97 (t, J=9.2 Hz, 2H), 7.88 (dd, J=8.4 Hz J=1.6 Hz, 1H), 7.64-7.56 (m, 2H), 7.10 (d, J=8.4 Hz, 1H), 6.69 (d, J=6.0 Hz, 1H), 6.60 (t, J=8.4 Hz, 1H), 6.59 (dd, J=8A Hz J=2.4 Hz, 1H), 5.06-4.97 (m, 1H), 3.67 (s, 3H), 3.59 (d, J=15.6 Hz, 1H), 3.51 (d, J=15.6 Hz, 1H), 3.02 (q, J=6.4 Hz, 2H), 2.31 (s, 3H), 2.06-1.90 (m, 2H), 1.50-1.16 (m, 4H). MS (ES⁺) $C_{31}H_{34}N_6O_4$ requires: 554, found. 555 (M+H)⁺.

EXAMPLE 4

2-{(1S)-1-{[(5-methoxy-2-methyl-1H-indol-3-yl)acetyl]amino}-5-[(1-oxidopyridin-2-yl)amino]pentyl}-5-(2-naphthyl)-1H-imidazol-3-ium bis(trifluoroacetate)

To a stirred solution (0.02 M) of the product from example 1 step 4 in 1-butanol, NaHCO₃ (4 eq.) and 2-bromopyridine-1-oxide (2 eq.) were added. The reaction mixture was heated to 100° C. for 48 h. After cooling down, it was diluted with brine and extracted with EtOAc. The combined organic layers were dried. Evaporation of the solvent gave a crude product that was purified by RP-HPLC (Waters X-TERRA MS C18, 5 micron, 19×100 mm; flow: 20 mL/min; Gradient: A: H₂O+ 0.1% TFA; B: MeCN+0.1% TFA; 80% A isocratic for 1 min, linear to 20% A in 9 min) to yield (4%) the title compound as a solid. ¹H NMR (400 MHz, DMSO d₆, 300K) δ 10.63 (s, 1H), 8.64 (d, J=6.6 Hz, 1H), 8.33 (s, 1H), 8.18 (d, J=6.6 Hz, 1H), 8.14 (s, 1H), 8.05 (d, J=8.8 Hz, 1H), 8.05-7.85 (m, 3H), 7.73-7.53 (m, 3H), 7.50-7.36 (m, 1H), 7.10 (d, J=8.8 Hz, 1H), 6.99 (s, 1H), 6.86 (d, J=8.3 Hz, 1H), 6.75-6.55 (m, 2H), 5.13-5.00 (m, 1H), 3.66 (s, 3H), 3.62-3.47 (m, 2H), 3.25-3.13 (m, 2H), 2.31 (s, 3H), 2.02-1.92 (r, 2H), 1.62-1.48 (m, 2H), 1.46-1.20 (m, 2H). MS (ES⁺) $C_{35}H_{36}N_6O_3$ requires: 588, found: 589 (M+H)⁺.

The following Examples were prepared according to the procedures described in Examples 1 to 3.

| Example | Compound Name | Molecular Ion [M + H]⁺ | Procedure |
|---|---|---|---|
| 5 | N-{(1S)-5-amino-1-[5-(2-naphthyl)-1H-imidazol-2-yl]pentyl}-2-(5-methoxy-2-methyl-1H-indol-3-yl)acetamide | 496 | Example 1 |
| 6 | 2-{(1S)-1-{[(5-methoxy-2-methyl-1H-indol-3-yl)acetyl]amino}-5-[(2-thienylcarbonyl)amino]pentyl}-5-(2-naphthyl)-1H-imidazol-3-ium trifluoroacetate | 606 | Example 1 |
| 7 | 2-((1S)-5-[(2-ammoniobenzoyl)amino]-1-{[(5-methoxy-2-methyl-1H-indol-3-yl)acetyl]amino}pentyl)-5-(2-naphthyl)-1H-imidazol-3-ium bis(trifluoroacetate) | 615 | Example 1 |
| 8 | 2-((1S)-5-[(methoxycarbonyl)amino]-1-{[(5-methoxy-2-methyl-1H-indol-3-yl)acetyl]amino}pentyl)-5-(2-naphthyl)-1H-imidazol-3-ium trifluoroacetate | 554 | Example 1 |
| 9 | 2-((1S)-1-{[(5-methoxy-2-methyl-1H-indol-3-yl)acetyl]amino}-5-{[(methylamino)carbonothioyl]amino}pentyl)-5-(2-naphthyl)-1H-imidazol-3-ium trifluoroacetate | 569 | Example 1 |
| 10 | 2-((1S)-5-({[(2-ammoniophenyl)amino]carbonyl}amino)-1-{[(5-methoxy-2-methyl-1H-indol-3-yl)acetyl]amino}pentyl)-5-(2-naphthyl)-1H-imidazol-3-ium bis(trifluoroacetate) | 630 | Example 1 |
| 11 | 2-((1S)-1-{[(5-methoxy-2-methyl-1H-indol-3-yl)acetyl]amino}-5-{[(propylamino)carbonyl]amino}pentyl)-5-(2-naphthyl)-1H-imidazol-3-ium trifluoroacetate | 581 | Example 1 |
| 12 | 2-((1S)-5-{[(butylamino)carbonyl]amino}-1-{[(5-methoxy-2-methyl-1H-indol-3-yl)acetyl]amino}pentyl)-5-(2-naphthyl)-1H-imidazol-3-ium trifluoroacetate | 595 | Example 1 |
| 13 | 2-((1S)-5-{[(ethylamino)carbonyl]amino}-1-{[(5-methoxy-2-methyl-1H-indol-3-yl)acetyl]amino}pentyl)-5-(2-naphthyl)-1H-imidazol-3-ium trifluoroacetate | 567 | Example 1 |

-continued

| Example | Compound Name | Molecular Ion [M + H]+ | Procedure |
|---|---|---|---|
| 14 | 2-ethyl-1-[3-({(1S)-5-{[(methylamino)carbonyl]amino}-1-[5-(2-naphthyl)-1H-imidazol-3-ium-2-yl]pentyl}amino)-3-oxopropyl]-1H-3,1-benzimidazol-3-ium bis(trifluoroacetate) | 552 | Example 2 |
| 15 | 2-((1S)-5-{[(methylamino)carbonyl]amino}-1-{[(2-oxoquinazolin-1(2H)-yl)acetyl]amino}pentyl)-5-(2-naphthyl)-1H-imidazol-3-ium trifluoroacetate | 538 | Example 2 |
| 16 | 2-((1S)-5-{[(methylamino)carbonyl]amino}-1-{[2-methyl-2-(methylammonio)propanoyl]amino}pentyl)-5-(2-naphthyl)-1H-imidazol-3-ium bis(trifluoroacetate) | 451 | Example 2 |
| 17 | 2-((1S)-5-[(aminocarbonyl)amino]-1-{[(5-methoxy-2-methyl-1H-indol-3-yl)acetyl]amino}pentyl)-5-(2-naphthyl)-1H-imidazol-3-ium trifluoroacetate | 539 | Example 1 |
| 18 | 2-((1S)-5-{[(methoxyamino)carbonyl]amino}-1-{[(5-methoxy-2-methyl-1H-indol-3-yl)acetyl]amino}pentyl)-5-(2-naphthyl)-1H-imidazol-3-ium trifluoroacetate | 569 | Example 3 |
| 19 | 2-((1S)-5-{[(ethoxyamino)carbonyl]amino}-1-{[(5-methoxy-2-methyl-1H-indol-3-yl)acetyl]amino}pentyl)-5-(2-naphthyl)-1H-imidazol-3-ium trifluoroacetate | 583 | Example 3 |

The invention claimed is:
1. A compound of formula I:

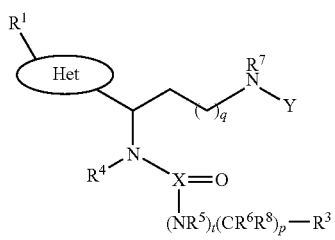

(I)

wherein:
p is 0, 1, 2 or 3;
q is 1, 2, 3 or 4;
t is 0 or 1;
X is C or S=O;
Y is $R^2$, (C=S)$R^2$, (C=O)$R^2$, (C=S)N$R^X R^2$ or (C=O)N$R^X R^2$;
Het is a 5 membered unsaturated heterocycle containing 1, 2, 3 or 4 heteroatoms independently selected from N, O and S, but not more than one of which is O or S;
optionally substituted by one or more groups independently chosen from cyano, halogen, hydroxy, oxido, oxo, nitro, amino, $C_{1-6}$alkylamino, di($C_{1-6}$alkyl)amino, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl and $C_{6-10}$aryl;

$R^1$ is naphthyl optionally substituted by one or more groups independently chosen from cyano, halogen, nitro, oxo, hydroxy, oxido, $C_{1-6}$alkyl, halo$C_{1-6}$alkyl, $C_{1-6}$alkoxy, halo$C_{1-6}$alkoxy, $C_{1-6}$alkylcarbonyl, $C_{6-10}$aryl, $C_{6-10}$aryloxy, $C_{6-10}$arylcarbonyl, N($R^a$)$_2$, SO$_2$N($R^b$)$_2$ and N($R^b$)SO$_2 R^b$;
$R^2$ is $R^9$ or $R^{10}$;
$R^3$ is hydrogen, halogen, hydroxy, cyano, $C_{1-6}$alkyl, halo$C_{1-6}$alkyl, hydroxy$C_{1-6}$alkyl, halo$C_{1-6}$alkoxy, $C_{3-10}$cycloalkyl, halo$C_{3-10}$cycloalkyl, $C_{2-10}$alkenyl, $C_{2-10}$alkynyl, nitro, N($R^c$)$_2$, $C_{6-10}$aryl, $C_{6-10}$aryl$C_{1-6}$alkyl, $C_{6-10}$aryl$C_{1-6}$alkoxy; 4, 5 or 6 membered saturated or partially saturated heterocycle containing 1, 2 or 3 heteroatoms independently selected from N, O and S, optionally bridged by a $C_{1-4}$alkyl group; 5 membered unsaturated heterocycle containing 1, 2, 3 or 4 heteroatoms independently selected from N, O and S, but not more than one of which is O or S; 6 membered unsaturated heterocycle containing 1, 2 or 3 nitrogen atoms; or a 7-13 membered saturated, partially saturated or unsaturated heterocycle containing heteroatoms independently selected from N, O or S; any of which rings being optionally substituted by one or more groups independently chosen from $R^d$;
$R^4$, $R^5$ and $R^7$ are independently selected from hydrogen and $C_{1-6}$alkyl;
$R^6$ and $R^8$ are independently hydrogen, $C_{1-6}$alkyl, a 5 or 6 membered saturated or partially saturated heterocycle containing 1, 2 or 3 heteroatoms independently selected from N, O and S or a 6 membered unsaturated heterocycle containing 1, 2 or 3 nitrogen atoms; each of which rings being optionally substituted by one or more groups independently chosen from halogen, nitro, amino, cyano, oxo, hydroxy, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl and $C_{2-6}$alkynyl; or $R^6$ and $R^8$ together represent an oxo group;

$R^9$ is hydrogen, hydroxy, $C_{1-6}$alkyl, halo$C_{1-6}$alkyl or $C_{1-6}$alkoxy;

$R^{10}$ is $C_{6-10}$aryl, $C_{6-10}$aryl$C_{1-6}$alkyl, a 5 membered unsaturated heterocycle containing 1, 2, 3 or 4 heteroatoms independently selected from N, O and S, but not more than one of which is O or S, or a 6 membered unsaturated heterocycle containing 1, 2, or 3 heteroatoms independently selected from N and O; optionally substituted by one or more groups independently chosen from cyano, halogen, hydroxy, oxo, oxido, nitro, $N(R^c)_2$, $C_{1-6}$alkyl, halo$C_{1-6}$alkyl, $C_{1-6}$alkoxy, halo$C_{1-6}$alkoxy, $C_{3-10}$cycloalkyl, $C_{2-6}$alkenyl, $C_{2-6}$alkynyl, $CON(R^b)_2$, $NR^bCOR^b$, $SO_2N(R^b)_2$, $NR^bSO_2R^b$, $C_{6-10}$aryl, 5 or 6 membered saturated or partially saturated heterocycle containing 1, 2 or 3 heteroatoms independently selected from N, O and S, 5 membered unsaturated heterocycle containing 1, 2, 3 or 4 heteroatoms independently selected from N, O and S, but not more than one of which is O or S, 6 membered unsaturated heterocycle containing 1, 2 or 3 nitrogen atoms and a 7-10 membered saturated, partially saturated or unsaturated heterocycle containing heteroatoms independently selected from N, O or S;

each $R^a$ is independently selected from hydrogen, $C_{1-6}$alkyl, $C_{6-10}$aryl, $C_{1-6}$alkylcarbonyl and $C_{6-10}$arylcarbonyl;

each $R^b$ is independently hydrogen, $C_{1-6}$alkyl, $C_{2-6}$alkenyl, $C_{2-6}$alkynyl, $C_{6-10}$aryl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo$C_{1-6}$alkoxy;

each $R^c$ is independently selected from hydrogen and $C_{1-6}$alkyl;

each $R^d$ is halogen, hydroxy, cyano, $C_{1-6}$alkyl, halo$C_{1-6}$alkyl, halo$C_{1-6}$alkylcarbonyl, halo$C_{1-6}$alkylcarbonyloxy, $C_{1-6}$alkoxy, halo$C_{1-6}$alkoxy, carboxy, $C_{1-6}$alkylcarbonyl, $C_{1-6}$alkoxycarbonyl, nitro, oxo, $SO_2N(R^e)_2$, $NR^eSO_2R^e$, $N(R^e)_2$, $C_{6-10}$aryl, $C_{6-10}$aryl$C_{1-6}$alkyl, 5 or 6 membered saturated or partially saturated heterocycle containing 1, 2 or 3 heteroatoms independently selected from N, O or S, optionally bridged by a $C_{1-4}$alkyl group; 5 membered unsaturated heterocycle containing 1, 2, 3 or 4 heteroatoms independently selected from N, O and S, but not more than one of which is O or S; or a 6 membered unsaturated heterocycle containing 1, 2 or 3 nitrogen atoms; any of which rings may be optionally substituted by one or more groups independently chosen from halogen, hydroxy, amino, cyano, $C_{1-6}$alkyl, halo$C_{1-6}$alkyl, $C_{1-6}$alkoxy and halo $C_{1-6}$ alkoxy;

each $R^e$ is independently hydrogen, $C_{1-6}$alkyl, $C_{1-6}$alkylcarbonyl, carboxy or $C_{1-6}$alkyloxycarbonyl; and each $R^x$ is independently selected from hydrogen and $C_{1-6}$alkyl;

provided that when Y is $R^2$ then $R^9$ is not hydrogen or $C_{1-6}$alkyl; and when Y is $(C=O)R^2$ then $R^9$ is not hydroxy or $C_{1-6}$alkoxy;

or a pharmaceutically acceptable salt, stereoisomer or tautomer thereof.

2. The compound according to claim 1 wherein:
Y is $R^{10}$, $(C=S)R^2$, $(C=O)R^{10}$, $(C=S)NR^xR^2$ or $(C=O)NR^xR^2$;
or a pharmaceutically acceptable salt, stereoisomer or tautomer therof.

3. The compound according to claim 1 wherein Y is $(C=O)NR^xR^2$.

4. The compound according to claim 1 of formula III:

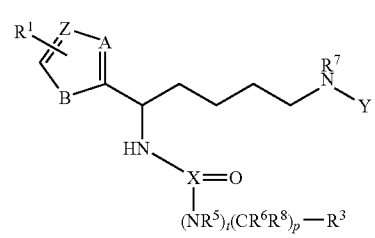

wherein:
$R^1$, $R^3$, $R^5$, $R^6$, $R^7$, $R^8$, X, Y, p and t are as defined in claim 2;
A represents CH or N;
B represents $NR^f$, O or S;
Z represents N or $CR^g$;
$R^f$ represents hydrogen or $C_{1-6}$alkyl; and
$R^g$ represents hydrogen, $C_{1-6}$alkyl or $C_{6-10}$aryl optionally substituted by up to two groups selected from halogen, cyano, $C_{1-6}$alkyl, $C_{1-6}$alkoxy, halo$C_{1-6}$alkyl or halo$C_{1-6}$alkoxy;
or a pharmaceutically acceptable salt, stereoisomer or tautomer thereof.

5. The compound according to claim 1 of formula V:

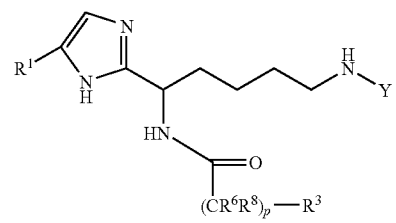

wherein $R^1$, $R^3$, $R^6$, $R^8$, Y and p are as defined in claim 2 or a pharmaceutically acceptable salt, stereoisomer or tautomer thereof.

6. A pharmaceutical composition comprising a compound according to claim 1, or a pharmaceutically acceptable salt, stereoisomer or tautomer thereof and a pharmaceutically acceptable carrier.

* * * * *